US012674178B2

(12) United States Patent
Aslanidi et al.

(10) Patent No.: US 12,674,178 B2
(45) Date of Patent: Jul. 7, 2026

(54) METHODS FOR THE EVALUATION OF NEUTRALIZING ANTIBODIES FOR ADENO-ASSOCIATED VIRUS

(71) Applicant: REGENTS OF THE UNIVERSITY OF MINNESOTA, Minneapolis, MN (US)

(72) Inventors: Georgiy Aslanidi, Minneapolis, MN (US); Karina Krotova, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 900 days.

(21) Appl. No.: 17/921,752

(22) PCT Filed: May 18, 2021

(86) PCT No.: PCT/US2021/032905
§ 371 (c)(1),
(2) Date: Oct. 27, 2022

(87) PCT Pub. No.: WO2021/236598
PCT Pub. Date: Nov. 25, 2021

(65) Prior Publication Data
US 2023/0167461 A1     Jun. 1, 2023

Related U.S. Application Data

(60) Provisional application No. 63/026,287, filed on May 18, 2020.

(51) Int. Cl.
*C12N 15/86* (2006.01)
*C12N 9/02* (2006.01)

(52) U.S. Cl.
CPC ........... *C12N 15/86* (2013.01); *C12N 9/0069* (2013.01); *C12N 2750/14143* (2013.01)

(58) Field of Classification Search
CPC ................................ C12N 15/86; C12N 15/63
See application file for complete search history.

(56) References Cited

PUBLICATIONS

Nicolson (J Virol. Jul. 27, 2016;90(16):7019-7031; doi: 10.1128/JVI.02953-15.).*
Krotova (2020, Human Gene Therapy, 31:19/20;1124-1131).*
Hao, PLoS One, Aug. 2008 I vol. 3 I Issue 8 I e2904, 8 pages.*
International Search Report and Written Opinion issued Sep. 14, 2021 in International Application No. PCT//US2021/032905, filed May 18, 2021; 10 pages.
International Preliminary Report on Patentability issued Dec. 1, 2022 in International Application No. PCT//US2021/032905, filed May 18, 2021; 8 pages.
Office Action issued Jan. 23, 2024, in European Application No. 21 734 968.7; 4 pages.
Aslanidi et al., Optimization of the capsid of recombinant adeno-associated virus 2 (AAV2) vectors: the final threshold? *PLoS One* 8, e59142 (2013).
Boutin et al., Prevalence of serum IgG and neutralizing factors against adeno-associated virus (AAV) types 1, 2, 5, 6, 8, and 9 in the healthy population: implications for gene therapy using AAV vectors. *Hum Gene Ther* 21, 704-712 (2010).
Calcedo et al., Humoral Immune Response to AAV. *Front Immunol* 4, 341 (2013).
Calcedo et al., Assessment of Humoral, Innate, and T-Cell Immune Responses to Adeno-Associated Virus Vectors. *Hum Gene Ther Methods* 29, 86-95 (2018).
Dasgupta et al., Compound C/Dorsomorphin: Its Use and Misuse as an AMPK Inhibitor. *Methods Mol Biol* 1732, 195-202 (2018).
Ding et al., Intracellular trafficking of adeno-associated viral vectors. *Gene Ther* 12, 873-880 (2005).
Dudek et al., An Alternate Route for Adeno-associated Virus (AAV) Entry Independent of AAV Receptor. *J Virol* 92, (2018).
Dudek et al., GPR108 Is a Highly Conserved AAV Entry Factor. *Mol Ther* 28, 367-381 (2020).
Falese et al., Strategy to detect pre-existing immunity to AAV gene therapy. *Gene Ther* 24, 768-778 (2017).
Farkas et al., A parvovirus isolated from royal python (*Python regius*) is a member of the genus *Dependovirus*. *J Gen Virol* 85, 555-561 (2004).
Gorovits et al., Recommendations for the Development of Cell-Based Anti-Viral Vector Neutralizing Antibody Assays. *AAPS J* 22, 24 (2020).
Guo et al., Rapid AAV-Neutralizing Antibody Determination with a Cell-Binding Assay. *Mol Ther Methods Clin Dev* 13, 40-46 (2019).
Halbert et al., Prevalence of neutralizing antibodies against adeno-associated virus (AAV) types 2, 5, and 6 in cystic fibrosis and normal populations: Implications for gene therapy using AAV vectors. *Hum Gene Ther* 17, 440-447 (2006).
Harbison et al., The parvovirus capsid odyssey: from the cell surface to the nucleus. *Trends Microbiol* 16, 208-214 (2008).
Havlik et al., Coevolution of Adeno-associated Virus Capsid Antigenicity and Tropism through a Structure-Guided Approach. *J Virol* 94, (2020).
High et al., rAAV human trial experience. *Methods Mol Biol* 807, 429-457 (2011).
Huttner et al., Genetic modifications of the adeno-associated virus type 2 capsid reduce the affinity and the neutralizing effects of human serum antibodies. *Gene Ther* 10, 2139-2147 (2003).
Jacobson et al., Improvement and decline in vision with gene therapy in childhood blindness. *N Engl J Med* 372, 1920-1926 (2015).
Jiang et al., Recent developments of biological reporter technology for detecting gene expression. *Biotechnol Genet Eng Rev* 25, 41-75 (2008).

(Continued)

*Primary Examiner* — Valarie E Bertoglio
(74) *Attorney, Agent, or Firm* — Mueting Raasch Group

(57) ABSTRACT

This disclosure describes a method that includes using dorsomorphin to increase the infectivity of adeno-associated virus (AAV). The AAV may be of any AAV serotype. In some embodiments, dorsomorphin may be used in combination with IL-6 or TNFα or both. This disclosure further describes methods for using dorsomorphin-treated cells to determine neutralizing antibody (NAb) titers.

17 Claims, 30 Drawing Sheets

(56)        References Cited

PUBLICATIONS

Judd et al., Random Insertion of mCherry Into VP3 Domain of Adeno-associated Virus Yields Fluorescent Capsids With No Loss of Infectivity. *Mol Ther Nucleic Acids* 1, e54 (2012).

Kay et al., Targeting photoreceptors via intravitreal delivery using novel, capsid-mutated AAV vectors. PLoS One 8, e62097 (2013).

Keeler et al., Recombinant Adeno-Associated Virus Gene Therapy in Light of Luxturna (and Zolgensma and Glybera): Where Are We, and How Did We Get Here? *Annu Rev Virol* 6, 601-621 (2019).

Kotterman et al., Engineering adeno-associated viruses for clinical gene therapy. *Nat Rev Genet* 15, 445-451 (2014).

Krotova et al., An Engineered AAV6-Based Vaccine Induces High Cytolytic Anti-Tumor Activity by Directly Targeting DCs and Improves Ag Presentation. *Mol Ther Oncolytics* 15, 166-177 (2019).

Landegger et al., A synthetic AAV vector enables safe and efficient gene transfer to the mammalian inner ear. *Nat Biotechnol* 35, 280-284 (2017).

Li et al., Neutralizing antibodies against adeno-associated virus examined prospectively in pediatric patients with hemophilia. *Gene Ther* 19, 288-294 (2012).

Li et al., Single amino acid modification of adeno-associated virus capsid changes transduction and humoral immune profiles. *J Virol* 86, 7752-7759 (2012).

Li et al., Development of Patient-specific AAV Vectors After Neutralizing Antibody Selection for Enhanced Muscle Gene Transfer. *Mol Ther* 24, 53-65 (2016).

Madigan et al., Ring finger protein 121 is a potent regulator of adeno-associated viral genome transcription. *PLoS Pathog* 15, e1007988 (2019).

Markusic et al., Evaluation of engineered AAV capsids for hepatic factor IX gene transfer in murine and canine models. *J Transl Med* 15, 94 (2017).

Meliani et al., Determination of anti-adeno-associated virus vector neutralizing antibody titer with an in vitro reporter system. *Hum Gene Ther Methods* 26, 45-53 (2015).

Mendell et al., Gene therapy for muscular dystrophy: lessons learned and path forward. *Neurosci Lett* 527, 90-99 (2012).

Mingozzi et al., Therapeutic in vivo gene transfer for genetic disease using AAV: progress and challenges. *Nat Rev Genet* 12, 341-355 (2011).

Mingozzi, AAV Immunogenicity: A Matter of Sensitivity. *Mol Ther* 26, 2335-2336 (2018).

Nathwani et al., Sustained high-level expression of human factor IX (hFIX) after liver-targeted delivery of recombinant adeno-associated virus encoding the hFIX gene in rhesus macaques. *Blood* 100, 1662-1669 (2002).

Nathwani et al., Adenovirus-associated virus vector-mediated gene transfer in hemophilia B. *N Engl J Med* 365, 2357-2365 (2011).

Nonnenmacher et al., Intracellular transport of recombinant adeno-associated virus vectors. *Gene Ther* 19, 649-658 (2012).

Ogden et al., Comprehensive AAV capsid fitness landscape reveals a viral gene and enables machine-guided design. *Science* 366, 1139-1143 (2019).

Pandya et al., Rationally designed capsid and transgene cassette of AAV6 vectors for dendritic cell-based cancer immunotherapy. *Immunol Cell Biol* 92, 116-123 (2014).

Pandya et al., Reprogramming Immune Response With Capsid-Optimized AAV6 Vectors for Immunotherapy of Cancer. *J Immunother* 38, 292-298 (2015).

Paulk et al., Bioengineered AAV Capsids with Combined High Human Liver Transduction In Vivo and Unique Humoral Seroreactivity. *Mol Ther* 26, 289-303 (2018).

Pekrun et al., Using a barcoded AAV capsid library to select for clinically relevant gene therapy vectors. *JCI Insight* 4, (2019).

Sayroo et al., Development of novel AAV serotype 6 based vectors with selective tropism for human cancer cells. Gene Ther 23, 18-25 (2016).

Smalley, First AAV gene therapy poised for landmark approval. *Nat Biotechnol* 35, 998-999 (2017).

Tse et al., Structure-guided evolution of antigenically distinct adeno-associated virus variants for immune evasion. *Proc Natl Acad Sci U S A* 114, E4812-E4821 (2017).

Wang et al., Prediction of adeno-associated virus neutralizing antibody activity for clinical application. *Gene Ther* 22, 984-992 (2015).

Warrington et al., Adeno-associated virus type 2 VP2 capsid protein is nonessential and can tolerate large peptide insertions at its N terminus. *J Virol* 78, 6595-6609 (2004).

Xiao et al., Disruption of Microtubules Post-Virus Entry Enhances Adeno-Associated Virus Vector Transduction. *Hum Gene Ther* 27, 309-324 (2016).

Yan et al., Ubiquitination of both adeno-associated virus type 2 and 5 capsid proteins affects the transduction efficiency of recombinant vectors. *J Virol* 76, 2043-2053 (2002).

Yates et al., Isolation and characterization of an Avian adenovirus-associated virus. *Infect Immun* 7, 973-980 (1973).

Zhong et al., Next generation of adeno-associated virus 2 vectors: point mutations in tyrosines lead to high-efficiency transduction at lower doses. *Proc Natl Acad Sci U S A* 105, 7827-7832 (2008).

* cited by examiner

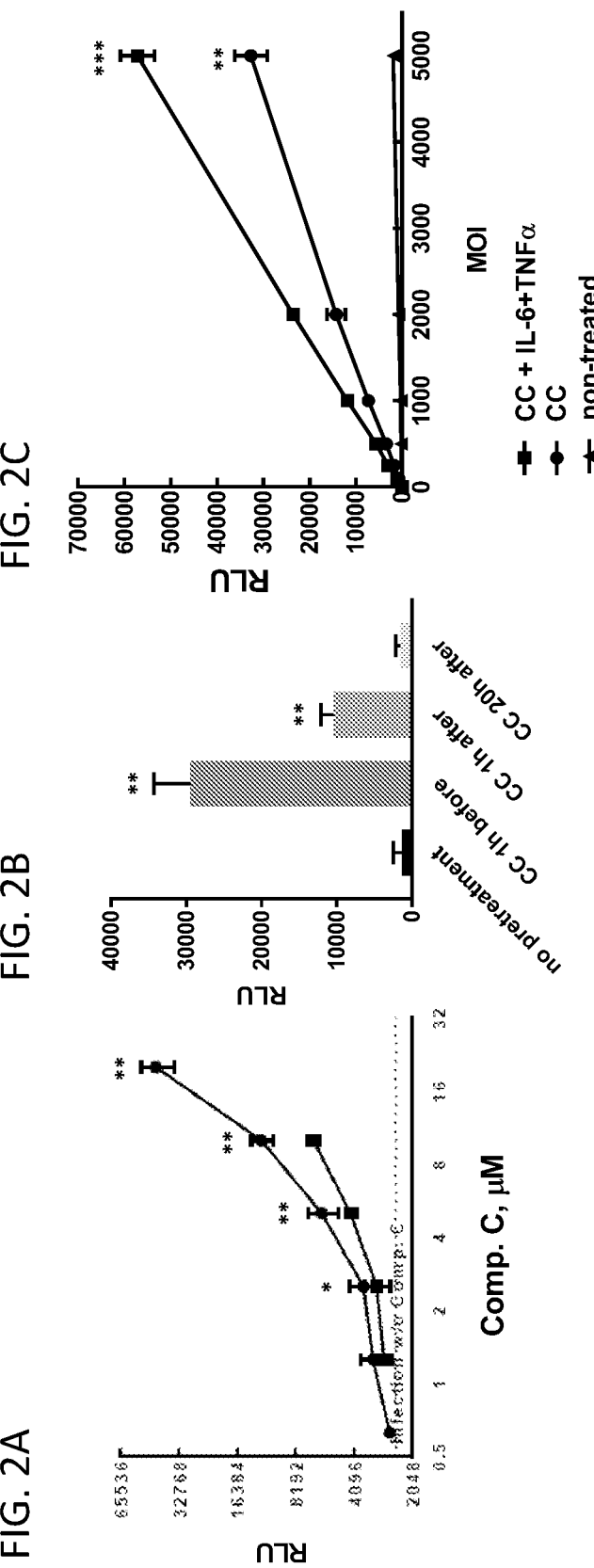

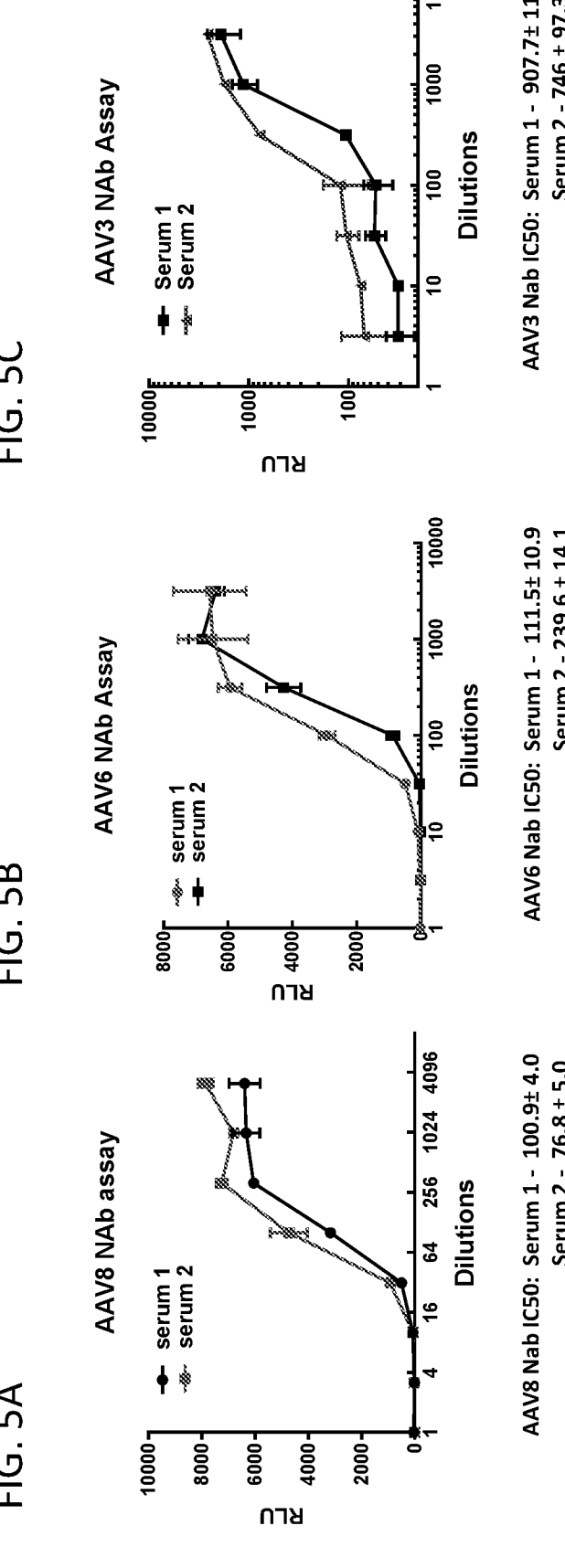

FIG. 7D
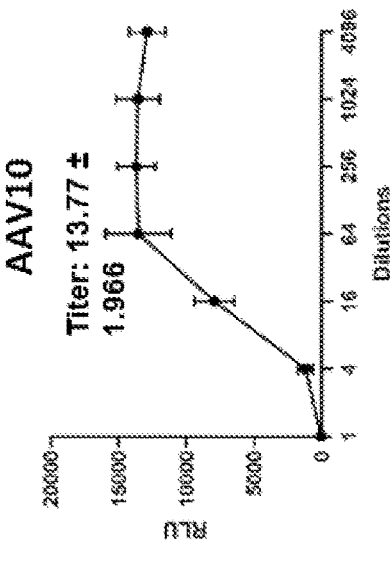
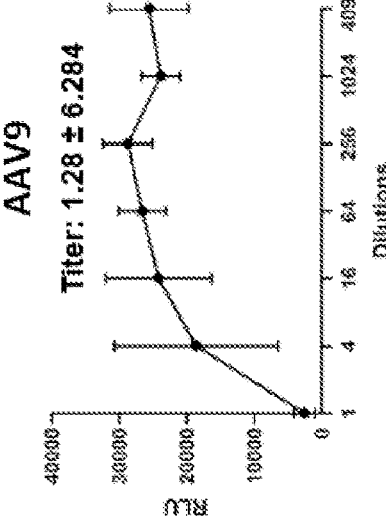
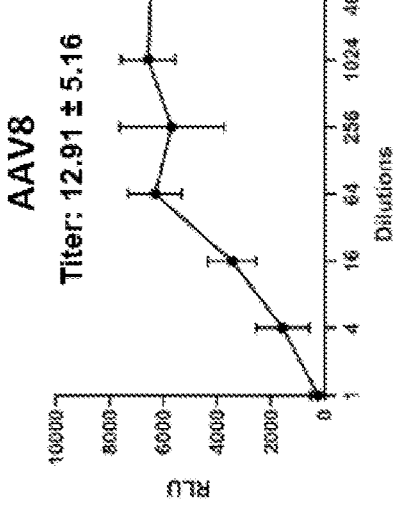
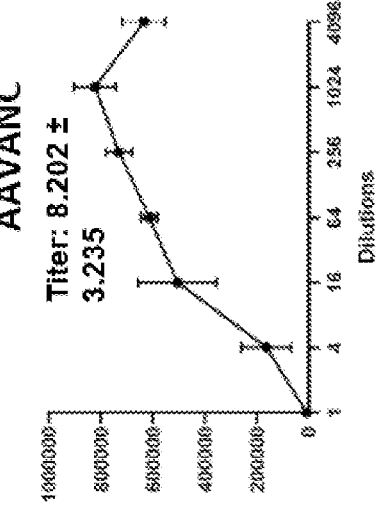

FIG. 7F
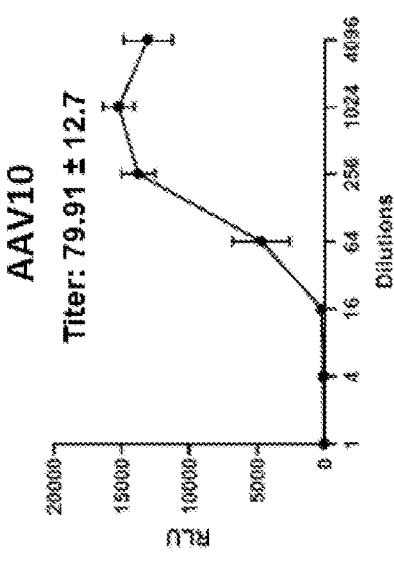
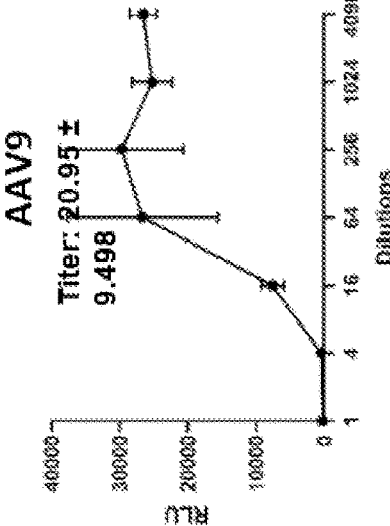
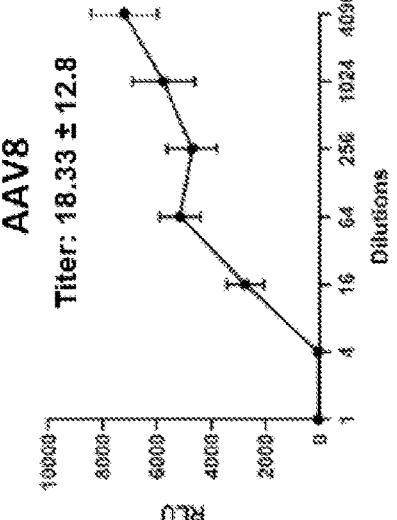
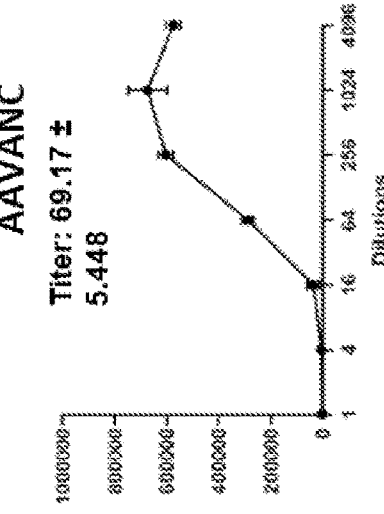

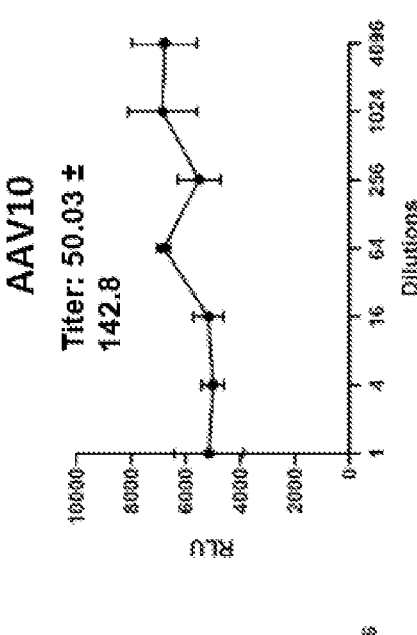
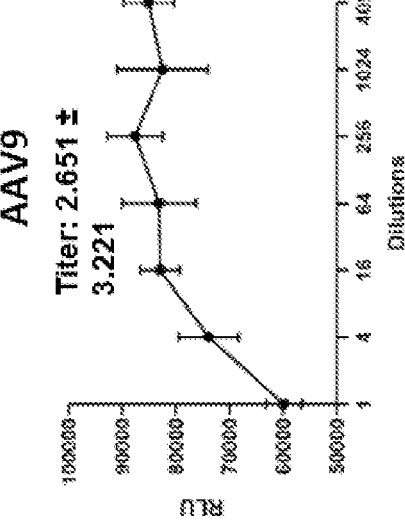
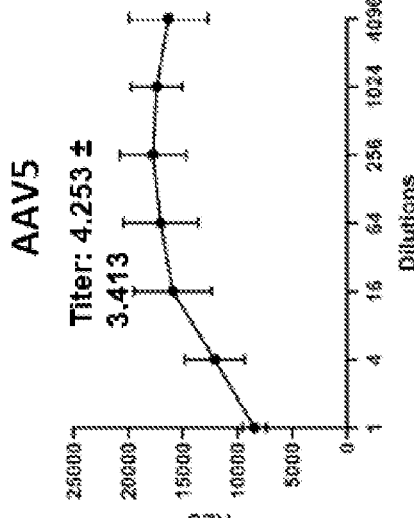
FIG. 8A

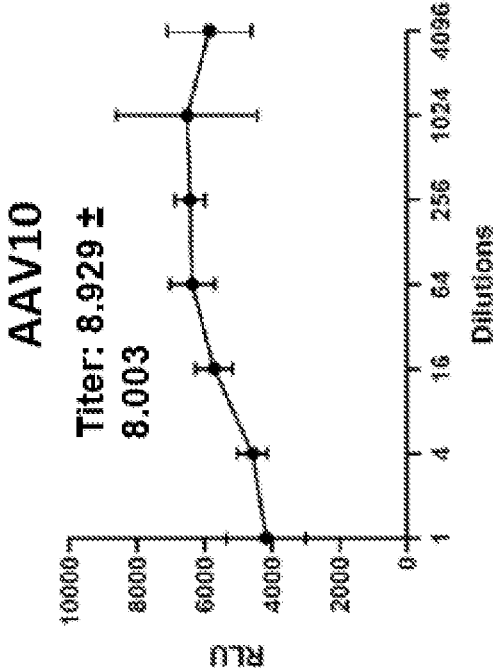
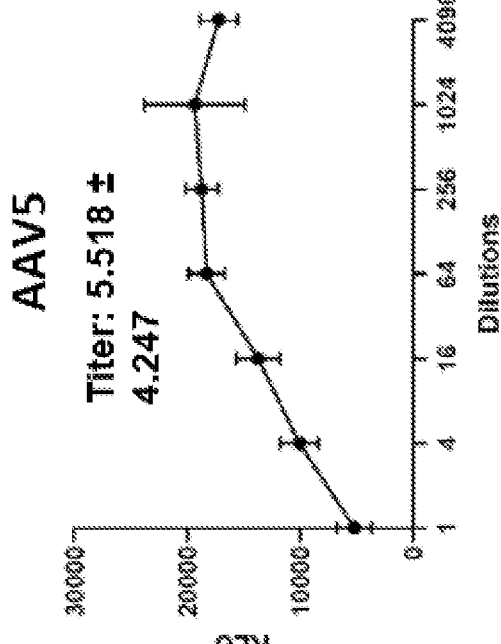
FIG. 8B

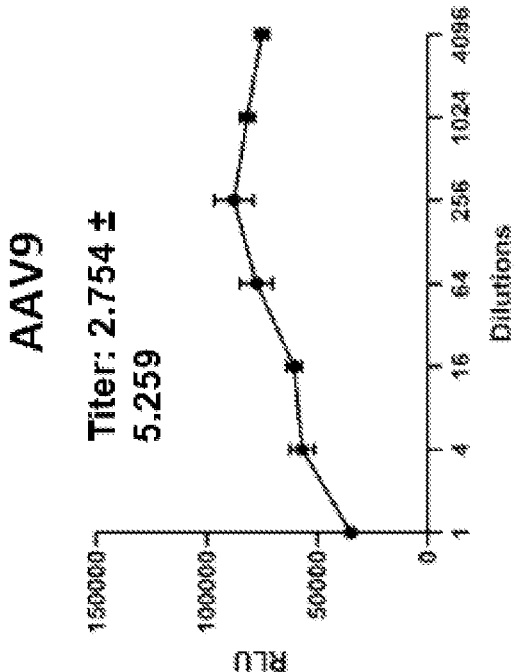
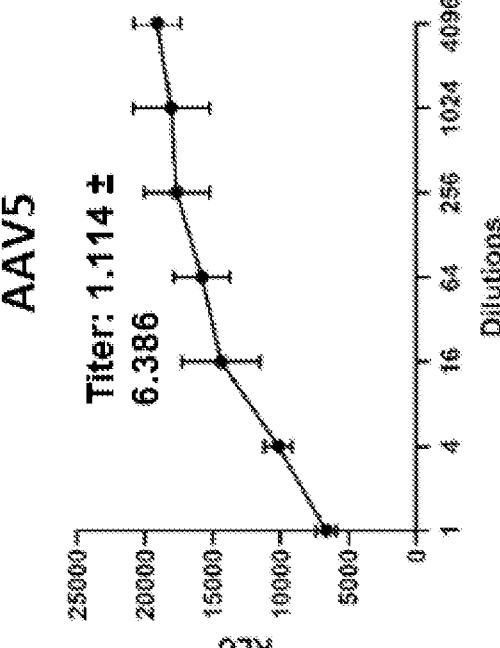
FIG. 8C

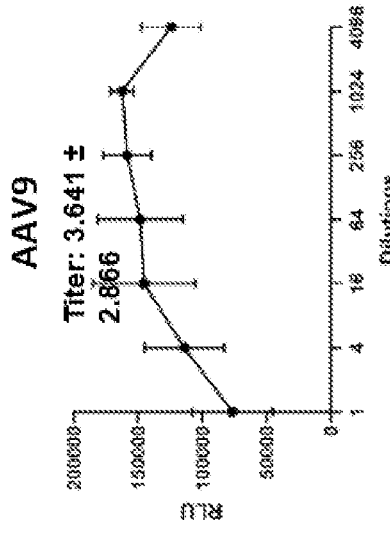
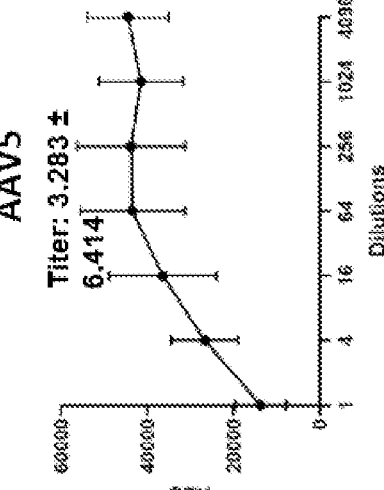
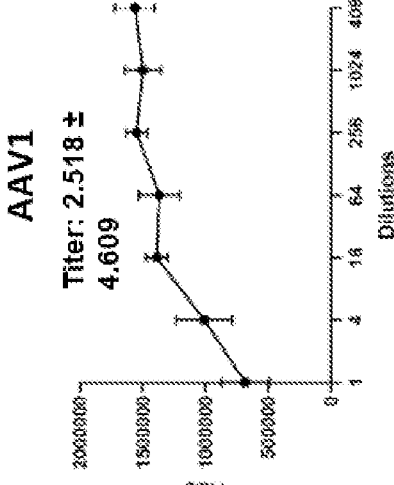
FIG. 8D

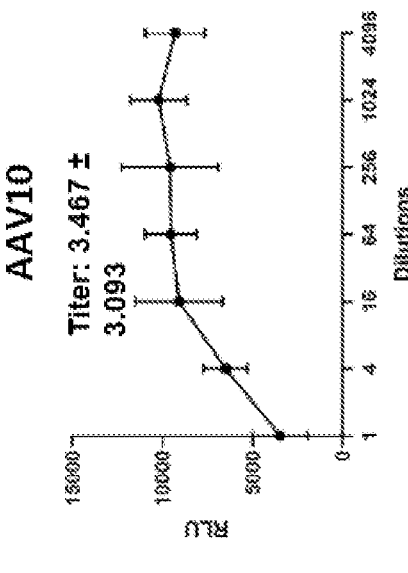
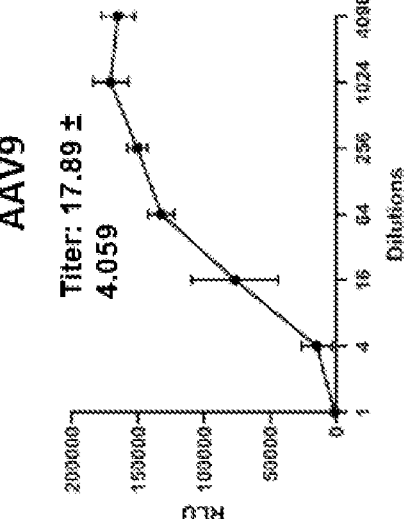
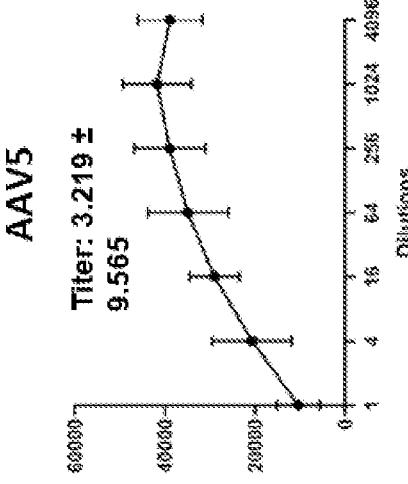
FIG. 8E

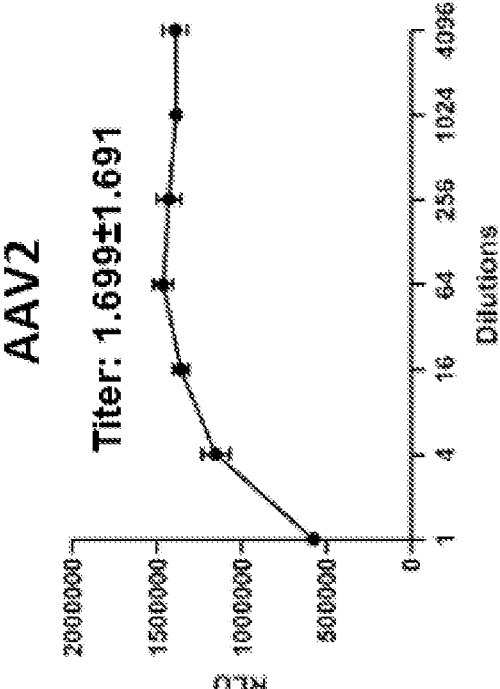
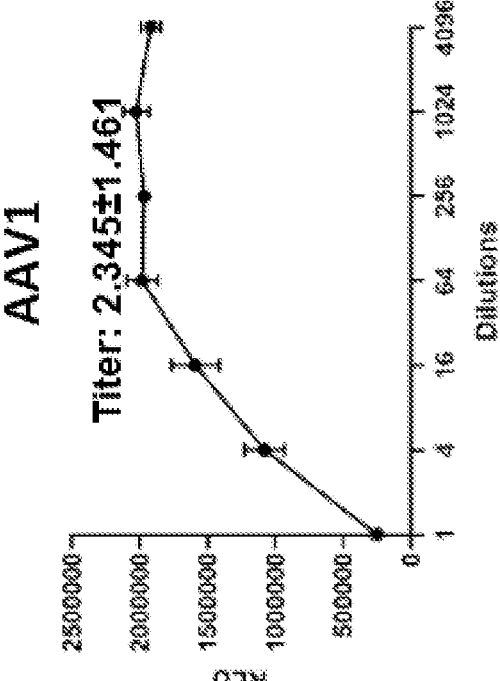
FIG. 9C

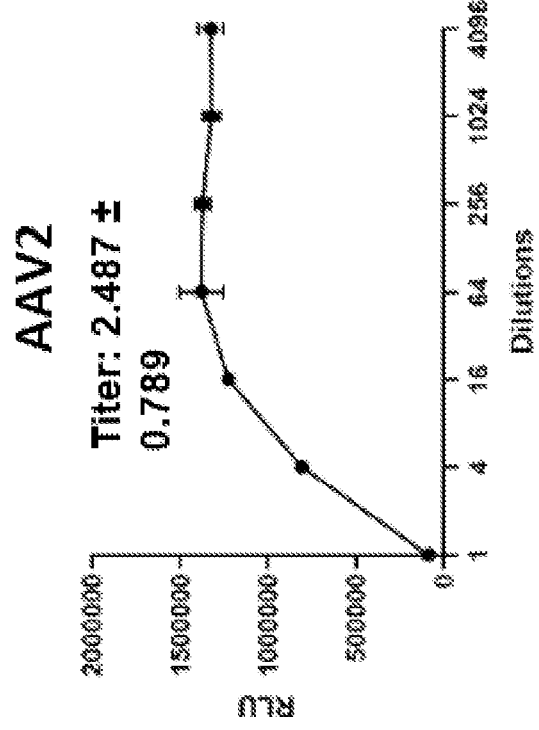
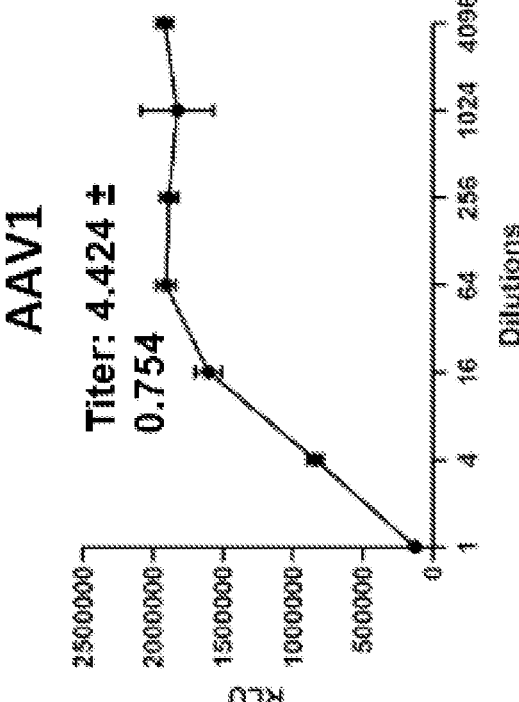
FIG. 9D

FIG. 10
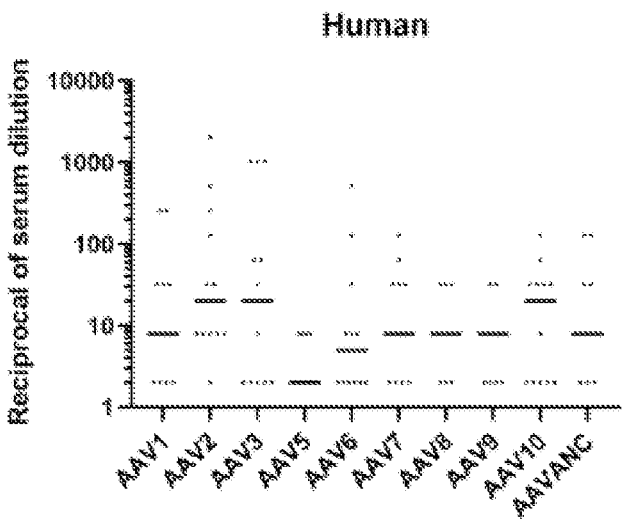
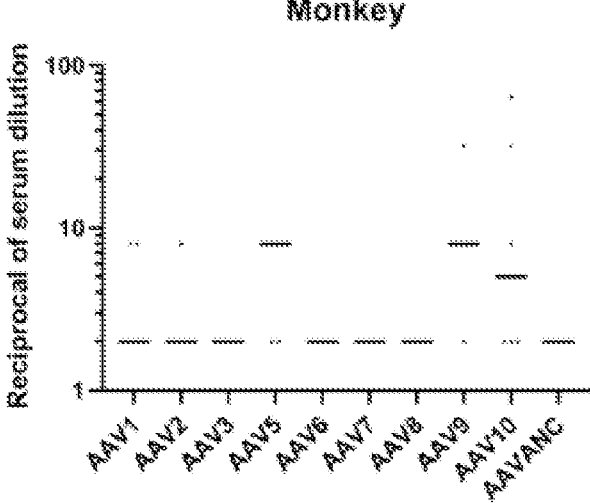
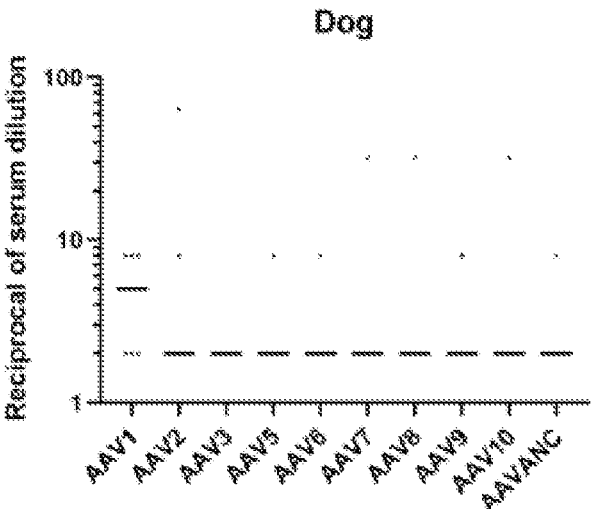

METHODS FOR THE EVALUATION OF NEUTRALIZING ANTIBODIES FOR ADENO-ASSOCIATED VIRUS

CROSS-REFERENCE TO RELATED APPLICATION

This application is the § 371 U.S. National Stage of International Application No. PCT/US2021/032905, filed May 18, 2021, which claims the benefit of U.S. Provisional Patent Application No. 63/026,287, filed May 18, 2020, each of which is incorporated herein by reference in its entirety.

GOVERNMENT FUNDING

This invention was made with government support under GM119186 awarded by the National Institutes of Health. The government has certain rights in the invention.

BACKGROUND

AAV-based gene therapy is currently being tested in about 50 clinical trials, and two AAV-based drugs have been approved by US FDA. But preexisting neutralizing antibodies to commonly-used AAV serotypes in patients limit the patient population that can benefit from the treatments. However, determining which patients have levels of preexisting neutralizing antibodies that would preclude treatment has proved challenging at least in part because several of the AAV serotypes useful for gene therapy are not infectious in vitro under normal conditions.

A reliable diagnostic to evaluate a patient's AAV seropositivity would be useful to assist in providing patients with effective AAV-mediated therapeutics.

SUMMARY OF THE INVENTION

This disclosure describes the discovery that the AMP-activated protein kinase (AMPK) inhibitor, dorsomorphin (also referred to herein as "Compound C" or "CC"), increases the infectivity of the most commonly used adeno-associated virus (AAV) serotypes in several different cell lines. This increased infectivity allows commonly used cell lines, including HEK293 cells, to be used to evaluate the presence and activity of neutralizing antibodies to AAV in a patient.

This disclosure further describes methods for using dorsomorphin-treated cells to determine neutralizing antibody (NAb) titers.

In one aspect, this disclosure describes a method that includes infecting a cell with adeno-associated virus (AAV) in the presence of dorsomorphin.

In some embodiments, the cell comprises a cell of a cell line. Exemplary cell lines include HEK293, HeLa, C2C12, Huh7, B16F10, or PC3.

In some embodiments, the AAV includes AAV1, AAV2, AAV3, AAV5, AAV6, AAV7, AAV8, AAV9, AAV10, AAV Anc80L65, or AAVKLK. In some embodiments, the AAV includes an AAV vector. The AAV vector may include a reporter gene. An exemplary reporter gene is a gene that expresses luciferase.

In some embodiments, dorsomorphin is added at least 10 minutes, at least 20 minutes, at least 30 minutes, at least 40 minutes, at least 50 minutes, at least 60 minutes, at least 90 minutes, or at least 120 minutes prior to the addition of AAV; and/or dorsomorphin is added up to 30 minutes, up to 40 minutes, up to 50 minutes, up to 60 minutes, up to 90 minutes, up to 120 minutes, up to 180 minutes prior to the addition of AAV.

In some embodiments, dorsomorphin is added to the cell at a concentration of at least 0.5 µM, at least 1 µM, at least 2 µM, at least 3 µM, at least 4 µM, at least 5 µM, at least 6 µM, at least 8 µM, at least 10 µM, or at least 15 µM; and/or dorsomorphin is added to the cell at a concentration of at up to 4 µM, up to 6 µM, up to 8 µM, up to 10 µM, up to 15 µM, up to 20 µM, or up to 30 µM.

In some embodiments, the method includes infecting the cell with AAV in the presence of IL-6 or TNFα or both.

In some embodiments, the method includes adding a composition to the dorsomorphin-treated cell at the time of infecting the cell with AAV, wherein the composition includes a composition known to comprise a neutralizing antibody (NAb) to AAV; or a composition being tested for the presence of a NAb to AAV. In some embodiments, the composition comprises serum including, for example, serum from a human or an animal. In some embodiments, the method includes adding multiple dilutions of the composition to dorsomorphin-treated cells at the time of infecting the cell with AAV.

In some embodiments, the method includes determining an NAb titer.

In some embodiments, the method includes measuring the level of the reporter gene expressed by the cell. In an exemplary embodiment, the reporter gene includes luciferase.

In some embodiments, the method includes adding multiple dilutions of the composition to dorsomorphin-treated cells at the time of infecting the cell with AAV, and determining the dilution at which 50% or greater inhibition of a reporter gene is observed.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

Unless otherwise specified, "a," "an," "the," and "at least one" are used interchangeably and mean one or more than one.

As used herein, the term "or" is generally employed in its usual sense including "and/or" unless the content clearly dictates otherwise.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

Herein, "up to" a number (for example, up to 50) includes the number (for example, 50).

The term "in the range" or "within a range" (and similar statements) includes the endpoints of the stated range.

For any method disclosed herein that includes discrete steps, the steps may be conducted in any feasible order. And, as appropriate, any combination of two or more steps may be conducted simultaneously.

All headings are for the convenience of the reader and should not be used to limit the meaning of the text that follows the heading, unless so specified.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." As used herein in connection with a measured quantity, the term "about" refers to that variation in the measured quantity as would be expected by the skilled artisan making the measurement and exercising a level of care commensurate with the objective of the measurement and the precision of the measuring equipment used. Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2A-FIG. 2C show pretreatment of HEK293 cells with CC significantly increased infectivity of AAV8/Luc. FIG. 2A. HEK293 were treated with different concentrations of CC either 1 hour before infection with AAV8/Luc at MOI=2,000 (circles) or 1 hour after infection with AAV8/Luc at MOI=2,000 (squares). Luciferase activity was measured 24 hours after infection with AAV8/Luc. * $p<0.05$ and  $p<0.01$, compared to luciferase activity in untreated cells. FIG. 2B. 10 µM CC was added to HEK293 at different times during infection with AAV8/Luc. Luciferase activity was measured 24 hours after infection with AAV8/Luc.  $p<0.01$, compared to luciferase activity in untreated cells. FIG. 2C. HEK293 were infected with different MOI (100-5,000) of AAV8/Luc in the presence of 10 µM CC or 10 µM CC+20 ng/ml TL-6+20 ng/ml TNFα (CC+TL-6+TNFα). Luciferase activity was measured 24 hours after infection with AAV8/Luc.  $p<0.01$ for all MOI in the presence of CC compared to infections without pre-treatment of HEK293, * $p<0.01$ for MOI in the range 500-5,000 in the presence of CC+IL-6+TNFα compared to the infections in the presence of CC. For MOI=250 $p<0.05$.

FIG. 3A. HEK293 were infected with different AAV/Luc serotypes at MOI 2000 in the presence of 10 µM CC, or CC+IL-6+TNFα. Luciferase activity was measured 48 hours later. For all serotypes, luciferase activity was higher in the presence of CC compared to non-treated cells ($p<0.01$). * $p<0.05$ and ** $p<0.01$ for cells infected in the presence of CC+IL6+TNFα compared to CC only. FIG. 3B. Luciferase activity of HEK293 infected with different AAV serotypes at MOI 2000 after 1 hour of pretreatment with 10 µM CC was measured 24 hours and 48 hours after infection. Cells were infected in the presence of CC as described in A. * $p<0.05$ and ** $p<0.01$ for 48 hours compared to 24 hours.

FIG. 5A-FIG. 5C show exemplary results of NAb assays for different AAV serotypes performed with HEK293 cells pretreated with CC, as described in Example 2. Plasma from mice infected with the indicated AAV serotype was assayed. FIG. 5A. NAb assay for AAV8. FIG. 5B. NAb assay for AAV6. FIG. 5C. NAb assay for AAV3.

FIG. 6A. Human sera from subjects 1-6. FIG. 6B. Human sera from subjects 7-12. FIG. 6C. Monkey sera. FIG. 6D. Dog sera.

FIG. 7A-J show anti-AAVs NAB titer determination for individual human samples and AAV serotypes. HEK293 cells pre-treated by Compound C were incubated with AAVs-Luc at MOI 2000 vg/cell and human sample serum.

Figures 1A, 1B:
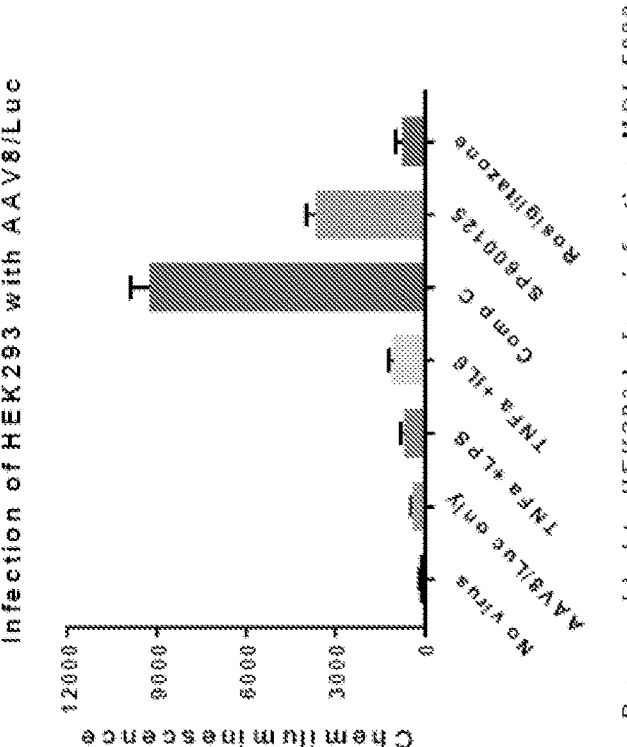
FIG. 1A-FIG. 1B show AMP-activated protein kinase (AMPK) inhibitor, dorsomorphin (also known as "Compound C" or "CC"), significantly enhanced the infection of HEK293 by AAV8 (FIG. 1A) and AAV2 (FIG. 1).

Luciferase activity was measured at 48 hours after AAV infection. Serum samples were diluted at 1:1, 1:4, 1:16, 1:64, 1:256, 1:1024, and 1:4096 for the assay. The Y-axis shows fluorescence intensity of luciferase. Neutralizing antibody titer was determined by the dilution of the serum sample at which 50% of the fluorescence signal is obstructed.

FIG. 8A-E show anti-AAVs NAB titer determination for individual monkey samples and AAV serotypes. HEK293 cells pre-treated by Compound C were incubated with AAVs-Luc at MOI 2000 vg/cell and monkey sample serum. Luciferase activity was measured at 48 hours after AAV infection. Serum samples were diluted at 1:1, 1:4, 1:16, 1:64, 1:256, 1:1024, and 1:4096 for the assay. The Y-axis shows fluorescence intensity of luciferase. Neutralizing antibody titer was determined by the dilution of the serum sample at which 50% of the fluorescence signal is obstructed.

FIG. 9A-E show anti-AAVs NAB titer determination for individual canine samples and particular AAV serotypes. HEK293 cells pre-treated by Compound C were incubated with AAVs-Luc at MOI 2000 vg/cell and canine sample serum. Luciferase activity was measured at 48 hours after AAV infection. Serum samples were diluted at 1:1, 1:4, 1:16, 1:64, 1:256, 1:1024, and 1:4096 for the assay. The Y-axis shows fluorescence intensity of luciferase. Neutralizing antibody titer was determined by the dilution of the serum sample at which 50% of the fluorescence signal is obstructed.

FIG. 10 shows the prevalence of serotype and species specificity in small group of human, monkeys, and dogs. Summary of prevalence of NABs against various AAV serotypes in serum samples from random human (n=12), monkey (n=6), and dog (n=6) naturally infected with AAV and measured by neutralizing antibody assay. The bar represents the median.

DETAILED DESCRIPTION OF ILLUSTRATIVE EMBODIMENTS

AAV in Gene Therapy

AAV is widely recognized as a safe and effective clinical-stage vector for gene therapy in a broad spectrum of inherited diseases such as Leber's congenital amaurosis, hemophilia A and B, and muscular dystrophy. For example, AAV-based treatments have been approved by the US FDA for use in two gene therapies: for a rare eye disease and for spinal muscular atrophy.

AAV-Capsid-Specific Neutralizing Antibodies

AAV seropositivity of the general patient population due to natural virus infection and the presence of neutralizing antibodies (NAb) in patients to commonly-used AAV serotypes limits the cohort of successful recipients of novel therapies.

Numerous attempts have been made to identify or develop novel AAV serotypes that can avoid neutralization. But even if an AAV capsid variants avoids neutralization in animal models, additional pre-clinical evaluation is required prior to use for human applications.

Methods for Evaluating the Presence and Activity of Neutralizing Antibodies to AAV at the Time of the Invention Several methods for determining neutralizing antibody (NAb) titer have been published, including an ELISA-based method (Nathwani et al., *Blood* 100:1662-1669 (2002)), a qPCR-based method for evaluating AAV binding to a cell (Guo et al., *Mol Ther Methods Clin Dev* 13:40-46 (2019)), a method that involves in vivo inhibition of AAV activity by injection of a test sample into C57BL/6 mice (Wang et al., *Gene Ther* 22:984-992 (2015)), a method that compares reporter gene activity delivered by AAV in the presence and absence of serum containing NAb (Falese et al., *Gene Ther* 24:768-778 (2017); Markusic et al., *J Transl Med* 15:94 (2017); and Meliani et al., *Hum Gene Ther Methods* 26:45-53 (2015)).

Some of the existing methods, such as measurements of NAb activity using mice, are time consuming and hard to standardize. Assays based on in vitro infection of cells with AAV-encoded reporter genes are more attractive because they are easier to establish and reproduce. However, no single cell line may be used for all commonly used AAV serotypes. Nor has a reporter gene with sufficient sensitivity to detect reliable differences between evaluated serum samples been identified.

For example, AAV8 is a highly efficient serotype for delivery of a transgene to the liver in vivo; however, AAV8—like AAV7, AAV9, and AAV10—exhibits low to no infectivity of cells in vitro. Infection of cells in cell culture, if possible at all, requires a very high multiplicity of infection (MOI).

In another example, although AAV1, AAV2, AAV5, and AAV6 infect cell in vitro, each requires a different cell line.

To address the limitation that no single cell line may be used for all commonly used AAV serotypes, a number of cell lines have been used (for example, HEK293, HeLa, Huh7, C2C12, etc.) for different AAV serotypes, a wide range of AAV MOIs are used, and a large selection of pharmacological drugs have been tested in an attempt to significantly enhance the transduction of AAV serotypes in vitro.

In some instances, a helper virus, such as adenovirus, has also been used to increase expression in AAV transduced cells. Alternatively, one non-commercially available cell line is made permissive for AAV infection by expressing the adenovirus E4 ORF gene under the control of the ecdysone-inducible promoter and ponasterone A (Meliani et al., *Hum Gene Ther Methods* 26:45-53 (2015)).

Methods of Using Dorsomorphin to Increase AAV Infectivity

In one aspect, this disclosure describes a method that includes using dorsomorphin (also referred to herein as "Compound C" or "CC") to increase the infectivity of adeno-associated virus (AAV).

As further described in the Examples, AMP-activated protein kinase (AMPK) inhibitor, dorsomorphin, increases the infectivity of the most commonly used adeno-associated virus (AAV) serotypes in several different cell lines. This increased infectivity allows commonly used cell lines, including HEK293 cells, to be used to evaluate the presence and activity of neutralizing antibodies to AAV in a patient.

The method may include infecting any suitable cell with AAV in the presence of dorsomorphin. The cell may include, for example, a cell of a cell line. Exemplary cell lines include HEK293, HeLa, C2C12, Huh7, B16F10, PC3, etc. In some embodiments, the cell may preferably include a cell from the HEK293 cell line.

The AAV may include any AAV serotype. In some embodiments, the AAV is preferably an AAV serotype useful for a pre-clinical or clinical application. In some embodiments, the AAV may include AAV1, AAV2, AAV3, AAV5, AAV6, AAV7, AAV8, AAV9, AAV10, AAV Anc80L65, or AAVKLK, or a combination thereof. In some embodiments, the AAV may include a sialic acid (SIA) binder (including, for example, AAV1, AAV4, AAV5, or AAV6). In some embodiments, the AAV may include a heparan sulfate proteoglycan (HSPG) binder (including, for example, AAV2, AAV3, AAV6, or AAV13). In some embodiments, the AAV may include a galactose binder (including, for example, AAV9). In some embodiments, the AAV may be derived from a recombinant library and/or a machine learning algorithm (e.g., as described in Kotterman et al., *Nat Rev Genet* 15:445-451 (2014); Paulk et al., *Mol Ther* 26:289-303 (2018); Ogden et al., *Science* 366:1139-1143 (2019); or Havlik et al., *J Virol.* 15; 94(19):e00976-20 (2020)), rationally designed to introduce one or more point mutations (e.g., as described in Zhong et al., *Proc Natl Acad Sci USA* 105(22):7827-7832 (2008); Markusic et al., *Mol Ther.* 18(12):2048-2056 (2010); Pandya et al., *Immunol Cell Biol.* 92(2):116-23 (2014); or Kay et al., *PLoS One* 8(4):e62097 (2013)), designed to possess a ligand or peptide insert (e.g., as described in Warrington et al., *J Virol* 78:6595-6609 (2004); Judd et al., *Mol Ther Nucleic Acids* 1:e54 (2012); or Sayroo et al., *Gene Ther* 23:18-25 (2016)), or isolated form different species (e.g., as described in Yates et al., *Infect Immun* 7(6):973-80 (1973) or Farkas et al *J Gen Virology* 85(3): 555-561(2004)).

In some embodiments, the AAV is preferably an AAV vector. In some embodiments, the AAV vector further includes a reporter gene. In some embodiments, the reporter gene preferably includes a gene that expresses luciferase. For example, in an exemplary embodiment, as described in the Examples, the AAV vector may express firefly luciferase (Luc) under the control of a promoter. Other exemplary reporter genes include, for example, genes that express GFP, YFP, mCherry, mApple, RFP, LacZ, creatine kinase, aequorin, *Renilla* luciferase, NANOLUC luciferase (Promega Corp., Madison, Wis.), *Gaussia* luciferase, luciferin (foxfire), etc. Exemplary suitable promoters include, but are not limited to, chicken β actin promoter, cytomegalovirus (CMV) promoter, elongation factor 1α (EF-1α) promoter, phosphoglycerate kinase (PGK) promoter, or a synthetic promoter (e.g., the CAG promoter).

In some embodiments, the method may include infecting a cell with AAV at a minimum multiplicity of infection (MOI) of at least 10 viral genomes (vg)/cell such as, for example, at least 50 vg/cell, at least 100 vg/cell, at least 200 vg/cell, at least 300 vg/cell, at least 400 vg/cell, at least 500 vg/cell or at least 1000, vg/cell. In some embodiments, the method may include infection a cell with AAV at a maximum MOI of no more than 500,000 vg/cell such as, for example, no more than 250,000 vg/cell, no more than 100,000 vg/cell, no more than 50,000 vg/cell, no more than 25,000 vg/cell, no more than 10,000 vg/cell, no more than 5,000 vg/cell, no more than 2,000 vg/cell, or no more than 1,000 vg/cell. The MOI is said to be "no more than" a reference MOI value when the MOI has a non-zero value up to the reference value.

The MOI also can be characterized by a range having endpoints defined by any a minimum MOI identified above and any maximum MOI identified above that is greater than the selected minimum MOI. For example, in some embodiments, the method may include infecting a cell with AAV at an MOI of from 100 to 5,000, from 200 to 2,000, from 100 to 10,000, from 1,000 to 5,000, from 1,000 to 2,000, etc.

In some embodiments, dorsomorphin may be added to the cell to be infected prior to the addition of AAV. For example, dorsomorphin may be added at least 10 minutes, at least 20 minutes, at least 30 minutes, at least 40 minutes, at least 50 minutes, at least 60 minutes, at least 90 minutes, or at least 120 minutes prior to the addition of AAV. In some embodiments, dorsomorphin may be added up to 30 minutes, up to 40 minutes, up to 50 minutes, up to 60 minutes, up to 90 minutes, up to 120 minutes, up to 180 minutes prior to the addition of AAV. In an exemplary embodiment, dorsomorphin is added at least 30 minutes and up to 90 minutes prior to the addition of AAV. In another exemplary embodiment, dorsomorphin is added 60 minutes and prior to the addition of AAV.

In some embodiments, dorsomorphin may be added to the cell to be infected prior to the addition of AAV at a concentration of at least 0.5 μM, at least 1 μM, at least 1.5 μM, at least 2 μM, at least 2.5 μM, at least 3 μM, at least 4 μM, at least 5 μM, at least 6 μM, at least 8 μM, at least 10 μM, or at least 15 μM. In some embodiments, dorsomorphin may be added to the cell to be infected prior to the addition of AAV at a concentration of at up to 4 μM, up to 6 μM, up to 8 μM, up to 10 μM, up to 15 μM, up to 20 μM, or up to 30 μM. In an exemplary embodiment, dorsomorphin may be added to the cell to be infected prior to the addition of AAV at a concentration of at least 2.5 μM and up to 20 μM. In at least one model system, a statistically significant increase in activity of AAV/Luc was observed when cells were pretreated with a CC concentration of at least 2.5 μM at concentrations higher than 20 μM CC became toxic to cells. In another exemplary embodiment, dorsomorphin may be added to the cell to be infected prior to the addition of AAV at a concentration of at least 5 μM and up to 15 μM. In a further exemplary embodiment, dorsomorphin may be added to the cell to be infected prior to the addition of AAV at a concentration of 10 μM.

In some embodiments, dorsomorphin may be present at the time the cell is infected with AAV at a concentration of at least 0.5 μM, at least 1 μM, at least 2 μM, at least 3 μM, at least 4 μM, at least 5 μM, at least 6 μM, at least 8 μM, at least 10 μM, or at least 15 μM. In some embodiments, dorsomorphin may be present at the time the cell is infected with AAV at a concentration of at a concentration of up to 4 μM, up to 6 μM, up to 8 μM, up to 10 μM, up to 15 μM, up to 20 μM, or up to 30 μM. In an exemplary embodiment, dorsomorphin may be present at the time the cell is infected with AAV at a concentration of at least 5 μM and up to 15 μM. In another exemplary embodiment, dorsomorphin may be present at the time the cell is infected with AAV at a concentration of 10 μM.

In some embodiments, an additional active agent may be added to the cell to be infected in addition to AAV. Exemplary additional active agents include IL-6 or TNFα or both. If included, the additional active agent may be used in any suitable amount. An additional active agent may be added at the same time as dorsomorphin or at a different time than dorsomorphin. For example, the additional active agent may be added at least 10 minutes, at least 20 minutes, at least 30 minutes, at least 40 minutes, at least 50 minutes, at least 60 minutes, at least 90 minutes, or at least 120 minutes prior to the addition of AAV. In some embodiments, the additional active agent may be added up to 30 minutes, up to 40 minutes, up to 50 minutes, up to 60 minutes, up to 90 minutes, up to 120 minutes, up to 180 minutes prior to the addition of AAV. In some embodiments, the additional active agent may be added at the same time as AAV.

In an exemplary embodiment, when the additional active agent includes IL-6, at least 5 ng/mL IL-6, at least 10 ng/mL IL-6, at least 15 ng/mL IL-6, or at least 20 ng/mL IL-6 may be added and/or up to 10 ng/mL IL-6, up to 15 ng/mL IL-6, up to 20 ng/mL IL-6, or up to 25 ng/mL IL-6 may be added. In another exemplary embodiment, 20 ng/mL IL-6 may be added.

In an exemplary embodiment, when the additional active agent includes TNFα, at least 5 ng/mL TNFα, at least 10 ng/mL TNFα, at least 15 ng/mL TNFα, or at least 20 ng/mL TNFα may be added and/or up to 10 ng/mL TNFα, up to 15 ng/mL TNFα, up to 20 ng/mL TNFα, or up to 25 ng/mL TNFα may be added. In another exemplary embodiment, 20 ng/mL TNFα may be added.

In yet another exemplary embodiment, 20 ng/mL IL-6 and 20 ng/mL TNFα may be added.

Methods of Using Dorsomorphin-Treated Cells in a Neutralizing Antibody Assay

This disclosure further describes methods for using a dorsomorphin-treated cell to determine the presence of a neutralizing antibody (NAb). In some embodiments, determining the presence of a neutralizing antibody includes determining a neutralizing antibody titer.

In an exemplary embodiment, the method includes adding a composition to the dorsomorphin-treated cell at the time of infecting the cell with AAV. The composition may include a composition known to include a NAb to AAV or a composition being tested for the presence of a NAb to AAV.

In some embodiments, the composition includes serum. The serum may be from a human or an animal. Exemplary animals include research animals such as humans, rat, mice, pigs, dogs, horses, etc. Canines are commonly used as a pre-clinical model for evaluating safety and efficacy of AAV-based drugs. AAV-based gene therapy treatments for hemophilia, muscular dystrophies, and vision have used dogs in preclinical studies prior to human use. Non-human primates (NHPs) are another common pre-clinical animal model for evaluating safety and efficacy of AAV-based drugs. Non-human primates are the closest genetic relatives to humans and possess similarities to humans in anatomy, cell physiology, and immunology.

In some embodiments, a composition that includes an AAV neutralizing antibody may include serum. The serum may be from a human or an animal known to be infected with AAV, including, for example, a human or an animal known to be infected with a particular AAV serotype.

In some embodiments, a composition being tested for the presence of a NAb to AAV may include serum from a patient. An exemplary patient is a person identified as likely to benefit from a particular AAV-based gene therapy. When the AAV-based gene therapy includes a particular AAV serotype, the patient's serum may be tested for the presence of NAb specific to that AAV serotype.

In some embodiments, including, for example, when determining an NAb titer is desired, a range of dilutions of the composition may be added dorsomorphin-treated cells at the time of infecting the cell with AAV.

In some embodiments, when the AAV vector further includes a reporter gene, a method for determining an NAb titer includes measuring the level of the reporter gene expressed by the cell. In some embodiments, the level of the reporter gene may be measured at least 6 hours, at least 12 hours, at least 18 hours, at least 24 hours, at least 30 hours, at least 36 hours, at least 42 hours, or at least 48 hours after infection of the cell with AAV. In some embodiments, the level of the reporter gene may be measured up to 12 hours, up to 18 hours, up to 24 hours, up to 30 hours, up to 36 hours, up to 42 hours, up to 48 hours, or up to 72 hours after infection of the cell with AAV. Increased incubation time (for example, to at least 48 hours) may be particularly beneficial for hard-to infect serotypes such as AAV3, AAV5, AAV10, or AAV8.

In an exemplary embodiment, as described in Example 2, the NAb titer of the composition may be determined by ascertaining the first dilution at which 50% or greater inhibition of the reporter gene is observed.

In another exemplary embodiment, also described in Example 2, the NAb titer may be quantified using GraphPad Prizm or any other suitable software from an inhibition exhibiting well-defined plateaus at minimum and maximum dilutions of the composition.

The present invention is illustrated by the following examples. It is to be understood that the particular examples, materials, amounts, and procedures are to be interpreted broadly in accordance with the scope and spirit of the invention as set forth herein.

EXAMPLES

All reagents, starting materials, and solvents used in the following examples were purchased from commercial suppliers (such as Sigma Aldrich, St. Louis, Mo.) and were used without further purification unless otherwise indicated.

Example 1

AAV8-Luciferase (Luc) or AAV2-Luc contain a single-strain expression cassette with chicken-b-actin promoter (CB)-driven fusion of firefly luciferase (Luc) and yellow fluorescent protein (YFP) genes (Pandya et al., *J Immunother* 38:292-298 (2015); Sayroo et al., *Gene Ther* 23: 18-25 (2016)).

HEK293 cells were infected with AAV8-Luciferase (Luc) or AAV2-Luc at an MOI of 5000 in the presence of several pharmacologically active drugs (TNFα+LPS, TNFα+IL-6, dorsomorphin (also known as "Compound C" or "CC"), SP600125, or rosiglitazone). The drugs were added 1 hour before injection with AAV-Luc. 24 hours after AAV-Luc was added, luciferase was detected, as further described in Example 2.

Results are shown in FIG. 1A-FIG. 1B and FIG. 6A-6D.

The AMP-activated protein kinase (AMPK) inhibitor, dorsomorphin, significantly enhanced the infection of HEK293 by AAV2 and AAV8 without cytotoxic effects.

Example 2

This Example describes a method for measuring of the titer in serum (from a subject—including, for example, from a mouse) of a neutralizing antibody (NAb) to an particular AAV serotype.

Materials:

| Reagents | Supplier |
|---|---|
| Compound C in solution | EMD Biosciences, 171261 |
| 293 T cell line | ATCC |
| Fetal Bovine Serum | Thermo Fisher (Gibco), 16000044 |
| DMEM (Dulbecco's Modified Eagle Medium) | Thermo Fisher (Gibco), 11965084 |
| Reporter AAV/Luciferase stocks | Sayroo et al.,Gene Ther. 23:18-25 (2016) |
| Bright-Gio ™ Luciferase Assay System | Promega, E2610, E2620, E2650 |
| Trypsin-EDTA (0.05%), phenol red | Thermo Fisher (Gibco), 25300120 |
| PBS | Thermo Fisher (Gibco), 20012027 |

-continued

| Reagents | Supplier |
|---|---|
| Complete media (also referred to herein as complete DMEM culture medium) | DMEM supplemented with 10% heat-inactivated FBS and 1% penicillin/streptomycin |

Method:

Day 0:

1. Remove culture medium (DMEM supplemented with 10% heat-inactivated FBS and 1% penicillin/streptomycin) from HEK293 cell culture, gently wash cells twice with 100 µL of PBS. Cells should be at low passage and approximately 80% confluent without being overgrown. Harvest cells by trypsinization and perform a cell count.

2. Resuspend cells in complete DMEM culture medium at 200,000 cells/mL. Seed cells in 96-well plates with black or white walls and clear bottoms: 20,000 cells/ well in 100 µL of complete media.

3. Incubate cells overnight in C02 incubator at 37° C.

Day 1:

1. Confirm microscopically that cells are 50-80% confluent.

2. Activate cells by adding 50 µL/well of warmed (37° C.) serum-free DMEM containing 30 µM CC (final concentration of CC: 10 µM).

3. Incubate in $CO_2$ incubator at 37° C. for one hour.

4. Prepare serial dilutions of test samples (for example, mouse or human serum) using HI-FBS as the diluent in a U-bottomed or V-bottomed 96-well plate. An exemplary dilution strategy is provided in Table 1.

4. Prepare a working solution of AAV. First, calculate the working concentration of AAV which is based on number of cells in well and multiplicity of infection (MOI) will be used.

For example, if on the day of infection cells are 50% confluent (assuming that 100% confluence consists of 50,000 cells/well) then in each well will be added AAV/Luc at MOI=2000 vg/well in 5 µl, the working virus concentration is calculated by following:

$$50{,}000*(\% \text{ confluence}/100)*MOI*(1000\ \mu l/5\ \mu l)=vg/ml$$

$$50{,}000*(50/100)*2{,}000*200=1\times10^{10}\ vg/ml\text{–working concentration of AAV/Luc}$$

For the whole 96-well plate, 800 µl of AAV/Luc plus extra is needed (if to mix 25 µl of AAV for each sample in triplicate, then 96 wells/3*25 µl=800 µl).

If the stock of AAV8/Luc is $1\times10^{12}$/ml, it should be diluted with PBS to a working concentration of $1\times10^{10}$/ ml (dilution factor 100), then for 1 mL of working concentration of AAV 10 µL of stock AAV-Luc should be diluted with 990 µL PBS.

5. Mix 25 µL of each dilution with 25 µL AAV-Luc (ratio 1:1) in a new U or V-bottomed 96-well plate and incubate for one hour at 37° C.

For the positive control, mix 25 µL AAV-Luc with 25 µL diluent.

For the negative control (background), mix 25 µl diluent (HI-FBS) with 25 µL PBS.

6. Add 10 µl per well of AAV/sample mix to the plate with HEK293 cells (pre-treated with CC). Each dilution was analyzed at least in triplicate. Positive control: maximum (MAX) infection level (AAV mixed with diluent HI-FBS); background: HI-FBS mixed with PBS (MIN) and no AAV. An exemplary plate layout is shown in Table 2.

7. Protect plate from light (for example, wrap the plate in aluminum foil) and incubate in $CO_2$ incubator at 37° C. for 24 hours.

Day 2

1. Thaw the Bright Glo Luciferase assay reagent at room temperature (18° C. to 25° C.) in the dark.

2. Remove media from the plate (for example, by quickly inverting the plate). Without washing the cells, add 50 µL of PBS per well.

3. Set up spectrophotometer to read chemiluminescence. If the spectrophotometer is BioTek the read conditions are: 500 ms, gain 125-135, height of plate 3.75 mm. Add 50 µL of Bright Glo substrate to each well, incubate plate 3 min in the dark and then read. For maximal light intensity, samples should be measured within 15 minutes of reagent addition.

TABLE 1

Preparation of the Dilution Cascade for the Test Samples

| Dilution factor | Volume of test sample | Volume of diluent (µl) |
|---|---|---|
| Dilution 1 1:1 | 40 µl of undiluted material | 0 |
| Dilution 2 1:4 | 10 µl of dilution 1 | 30 |
| Dilution 3 1:16 | 12 µl of dilution 2 | 30 |
| Dilution 4 1:64 | 12 µl of dilution 3 | 30 |
| Dilution 5 1:256 | 12 µl of dilution 4 | 30 |
| Dilution 6 1:1,024 | 12 µl of dilution 5 | 30 |
| Dilution 7 1:4.096 | 12 µl of dilution 6 | 30 |

Positive control: HI-FBS alone

TABLE 2

Example of assay plate layout:

| | | Sample 1 | | | Sample 2 | | | Sample 3 | | | Sample 4 | |
|---|---|---|---|---|---|---|---|---|---|---|---|---|
| | 1 | 2 | 3 | 4 | 5 | 6 | 7 | 8 | 9 | 10 | 11 | 12 |
| A | 1:1 | 1:1 | 1:1 | 1:1 | 1:1 | 1:1 | 1:1 | 1:1 | 1:1 | 1:1 | 1:1 | 1:1 |
| B | 1:4 | 1:4 | 1:4 | 1:4 | 1:4 | 1:4 | 1:4 | 1:4 | 1:4 | 1:4 | 1:4 | 1:4 |
| C | 1:16 | 1:16 | 1:16 | 1:16 | 1:16 | 1:16 | 1:16 | 1:16 | 1:16 | 1:16 | 1:16 | 1:16 |
| D | 1:64 | 1:64 | 1:64 | 1:64 | 1:64 | 1:64 | 1:64 | 1:64 | 1:64 | 1:64 | 1:64 | 1:64 |
| E | 1:256 | 1:256 | 1:256 | 1:256 | 1:256 | 1:256 | 1:256 | 1:256 | 1:256 | 1:256 | 1:256 | 1:256 |

TABLE 2-continued

| Example of assay plate layout: | | | | | | | | | | | |
| --- | --- | --- | --- | --- | --- | --- | --- | --- | --- | --- | --- |
| Sample 1 | | | Sample 2 | | | Sample 3 | | | Sample 4 | | |
| 1 | 2 | 3 | 4 | 5 | 6 | 7 | 8 | 9 | 10 | 11 | 12 |
| F 1:1,024 | 1:1,024 | 1:1,024 | 1:1,024 | 1:1,024 | 1:1,024 | 1:1,024 | 1:1,024 | 1:1,024 | 1:1,024 | 1:1,024 | 1:1,024 |
| G 1:4,096 | 1:4,096 | 1:4,096 | 1:4,096 | 1:4,096 | 1:4,096 | 1:4,096 | 1:4,096 | 1:4,096 | 1:4,096 | 1:4,096 | 1:4,096 |
| H MAX | MAX | MAX | MAX | MAX | MAX | MIN | MIN | MIN | MIN | MIN | MIN |

MAX—maximum AAV infection level: mixed with diluent (HI-FBS).
MIN—background levels (no AAV): HI-FBS mixed with PBS Calculation of Anti-AAV NAb Titer:

Method 1:

NAb titer is defined as the neutralizing titer of the sample is the first dilution at which 50% or greater inhibition of the luciferase expression is measured.

NAb titer may be quantified manually by subtracting the average background value from all measurements and then by calculating percent of the total luciferase expression according to the following formula:

appropriate inhibition curve being attained. The curve should have well-defined plateaus at minimum and maximum dilutions. When the values at the highest dilution of the tested sample are much lower than the maximum value, the assay should be repeated with additional points of diluted samples.

Exemplary Troubleshooting:

| PROBLEM | SOLUTION |
| --- | --- |
| High Variability in readout across triplicate wells | The major source of such variability is unequal number of cells in the different wells. HEK293 cells is readily detached from plate during trypsinization step, but don't dissociate easily from each other. Ensure that cells form a single cell suspension at step of plating. In addition, wrapping the plate in aluminum foil during incubation time in $CO_2$ incubator will help to maintain even temperature across the plate and as result more even growing. Since HEK293 cells detach easily, to prevent the loss of cells during the assay, avoid aspiration of media or plate washing. |
| Low level of luciferase readout | The aliquot of reporter AAV lost activity or the titer was miscalculated. Take another aliquot or re-titer virus. The quality of the HEK293 cells also very important. Cells should be of low passage and be 50-70% confluent at the beginning of experiment. To increase the signal for serotypes with low infectivity several approaches can be utilized. 1. Time of incubation can be extended from 24 to 48 h. 2. MOI can be increased. However, make sure that luciferase signal is dose dependent and is not saturated. 3. For many serotypes pre-treatment of HEK293 cells with CC together with IL-6 and TNFa will additionally increase the luciferase readout. |
| The RLU of MAX Luciferase signal is significantly lower than some of dilutions of test sample | FBS used as diluent inhibits AAV infection by itself. Different providers and lot of FBS should be tested on the ability to affect the AAV infectivity. |

Percent luciferase expression=[(test sample luciferase reading−no virus luciferase signal)/(max luciferase signal−no virus luciferase signal)]*100

The neutralizing titer of the sample is determined as the first dilution at which 50% or greater inhibition of the luciferase expression is measured. For example, if 50% or greater inhibition is observed at a 1:10 dilution of the sample, the titer is reported as 1:10.

Method 2:

Alternatively, NAb titer may be quantified using Graph-Pad Prizm or any other suitable software.

Put data as XY file, where X is a testing sample dilutions and Y-is luminescence measurements in triplicates. Then go to results folder to analyze data: use XY analysis→Nonlinear regression (curve fit)→[Agonist] vs. response→Variable slope (four parameters).

The software will calculate EC50 which corresponds to NAb titer. Note, that the use of this analysis depends on the Results and Discussion Briefly, AAV vectors used in this study (serotypes 1, 2, 3, 5, 6, 7, 8, 9, 10, and recently identified Anc80L65) (Landegger et al., Nat Biotechnol 35:280-284 (2017)) were packaged in HEK293 cells by triple transfection with polyethyleneimine (PEI) and isolated by iodixanol gradient followed by ion-exchange column purification as described (Krotova et al., Mol Ther Oncolytics 15:166-177 (2019); Pandya et al., Immunol Cell Biol 92:116-123 (2014)). The vectors contain a single-strain expression cassette with chicken-b-actin promoter (CB)-driven fusion of firefly luciferase (Luc) and yellow fluorescent protein (YFP) genes (Pandya et al., J Immunother 38:292-298 (2015); Sayroo et al., Gene Ther 23:18-25 (2016)).

First, escalation doses of CC were used to identify the optimal drug concentration for AAV serotype 8 (FIG. 2A). Pretreatment of HEK293 with CC dose-dependently increased luciferase activity 24 hours after infection. The 10 μM CC dose was selected for further experimentation because it was determined to be the minimal concentration that induces high AAV transduction: luciferase activity was five times higher compared to non-treated cells and values were two orders higher than background.

In the next step of protocol optimization, 10 μM CC was added to cells at different time points before or after AAV 8 infection. The maximum increase in AAV8-mediated luciferase expression was observed when cells were pre-treated one hour prior to infection with AAV (FIG. 2B). Hence, in all subsequent experiments HEK293 were pre-treated with 10 μM CC one hour before infection.

Next, escalating doses of AAV8-Luc in the presence of CC were used to demonstrate the linear dose-dependency of luciferase expression in an MOI range of 100 to 5000 viral genomes (vg)/cell. In addition, pre-treatment of cells with CC together with pro-inflammatory cytokines IL-6 (20 ng/ml) and TNFα (20 ng/ml) was found to further increased luciferase expression. It should be noted that without CC, treatment with IL-6 and TNFα only marginally increase luciferase expression.

Figures 3A, 3B:
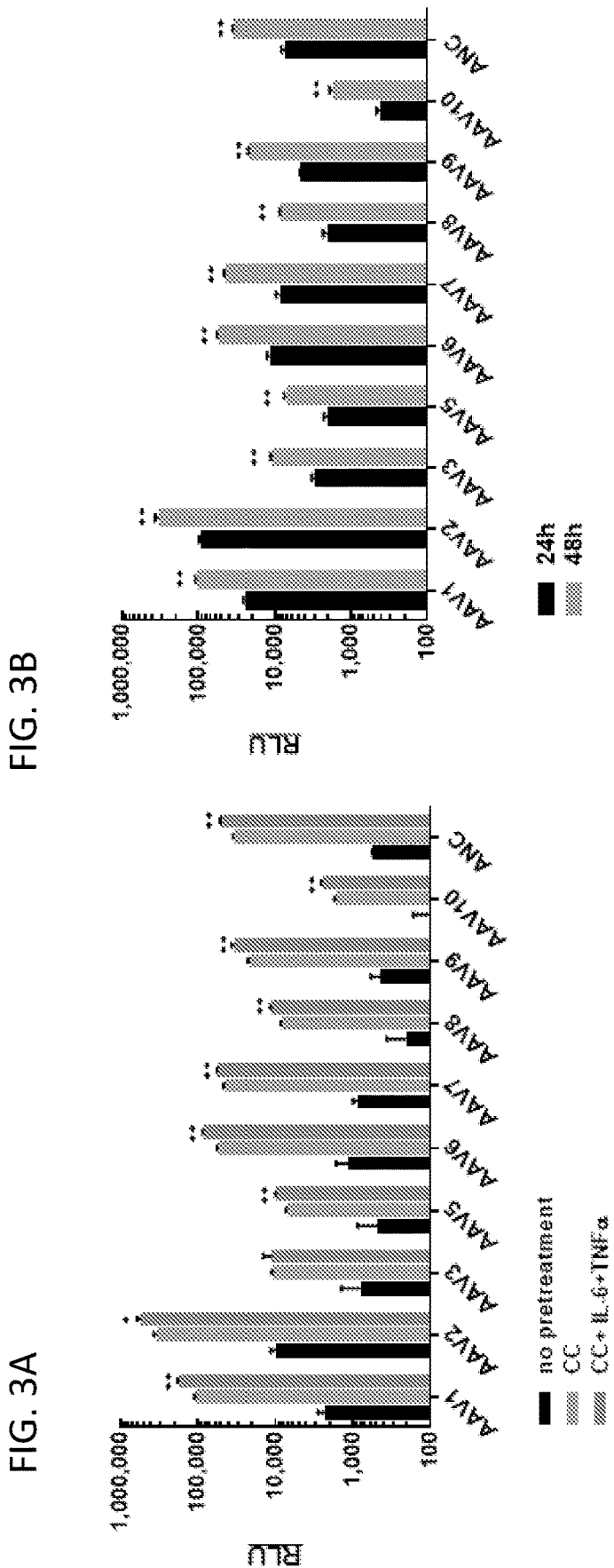
FIG. 3A-FIG. 3B show CC enhanced the infectivity of all tested AAV serotypes.

The dramatic improvement of AAV8 transduction in vitro in the presence of CC prompted test to determine if similar effect could be achieved for other AAV serotypes. The transduction efficiency of ten common AAV serotypes at MOI 2000 vg/cell was analyzed. Without pre-treatment with CC, only cells infected with AAV1 and AAV2 had luciferase activity significantly higher than background levels at 24 hours and 48 hours after infection (see FIG. 3A). Pre-treatment with CC, however, resulted in significantly increased levels of luciferase for all tested serotypes (FIG. 3A). In addition, extending incubation time after infection from 24 hours to 48 hours significantly increased luciferase activity for all serotypes (FIG. 3B). Increasing incubation time to 48 hours may be particularly beneficial for measurement NAb for hard-to infect serotypes such as AAV3, AAV5, AAV10, or AAV8.

For example, in the absence of pre-treatment with CC, the luciferase activity for AAV10 was at background levels and for AAV3, 5, 8 and 9 slightly higher than background levels, making it impossible to measure NAb titers for these serotypes. After pretreatment with CC, the levels of luciferase expression for these serotypes were high enough to measure NAb titers.

The highest luciferase activity after pre-treatment with CC was observed for AAV2 (more than 1000 times higher background in the presence of CC at 48 hours) and the lowest luciferase activity after pre-treatment with CC was observed for AAV10 (8 times higher background).

Addition of IL-6 and TNFα at the time of CC pre-treatment improved infection efficiency for all serotypes except AAV3 (FIG. 3A). Thus, additional treatment IL-6 and TNFα may be used for some serotypes (for example, AAV10) if pre-treatment with CC and/or an increase of MOI is inadequate to provide reporter gene activity sufficient for an NAb assay.

To ensure that the addition of CC is not affecting measurements of NAb titer, AAV2 NAb titer was determined with non-treated HEK293 cells and CC pre-treated HEK293 cells. Because AAV2 exhibited the highest infection rates of any serotype for HEK293 cells with without any additional stimulation of cells, AAV2 was selected for this experiment. Mouse serum from animals injected intramuscularly (i.m) with $10^{10}$ AAV2-Luc was analyzed by the protocol described above.

16

Figure 4:
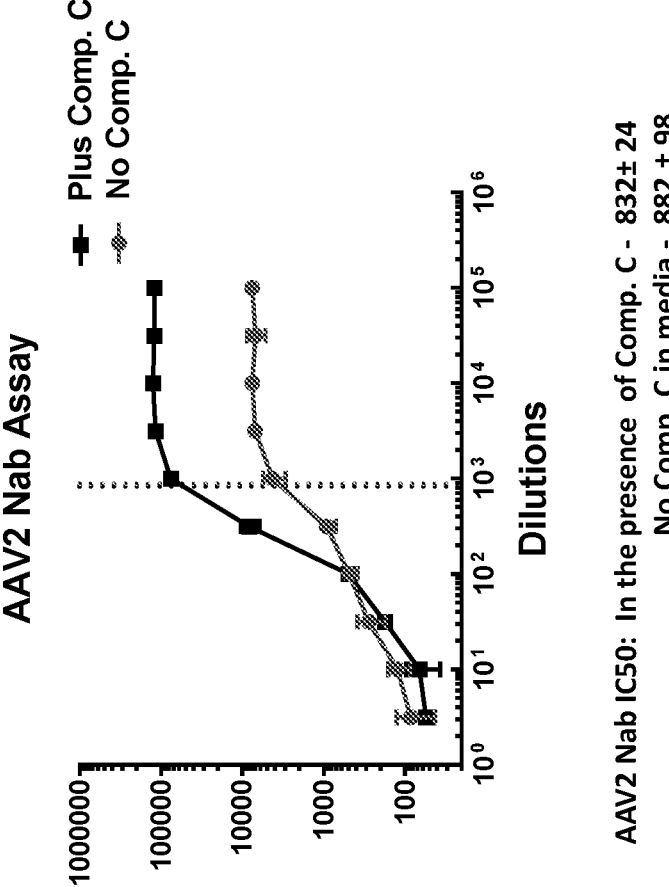
FIG. 4 shows a neutralizing antibody (NAb) assay conducted in the presence of CC did not affect the value of NAb titer. Mouse plasma was collected 1 month after injection with AAV2 and analyzed for the presence of NAb by using HEK293 cells either pre-treated or non-treated with CC. While CC significantly increased the values for Luciferase activity, it did not affect NAb titer (as demonstrated by overlaid vertical dotted lines corresponded to NAb titers for AAV2 measured in the presence and absence of CC). The difference in NAb titer was not statistically significant.
Figure 6A:
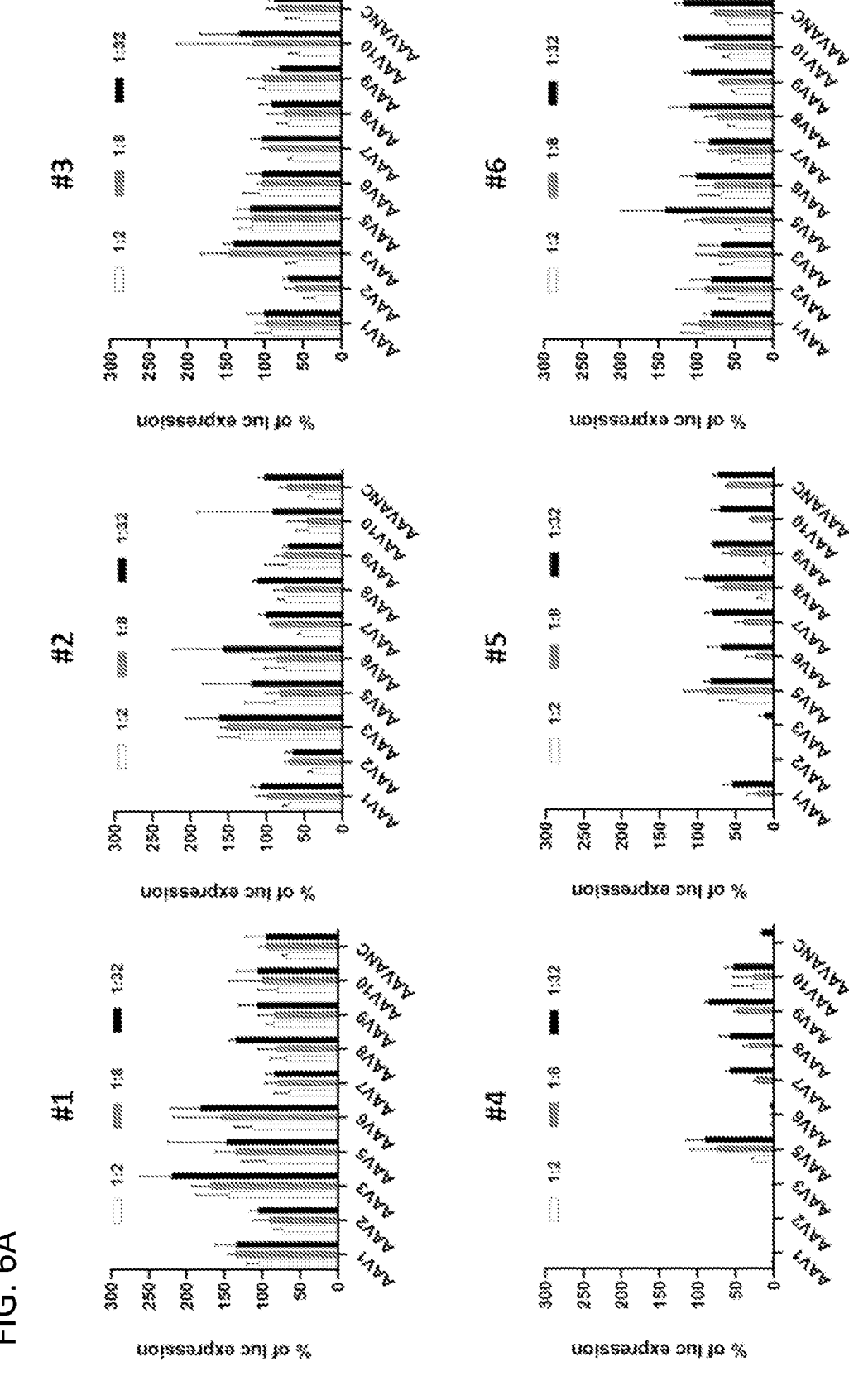
FIG. 6A-FIG. 6D show the results of anti-AAVs neutralizing antibody screening assays. HEK293 cells pre-treated by Compound C were incubated with AAVs-Luc at MOI 2000 vg/cell the serum from human, monkey, and canine subjects. Luciferase activity was measured at 48 hours after AAV infection. Serum samples were diluted at 1:2, 1:8, and 1:32 and used for the assay. The Y-axis shows percentage of luciferase expression, relative to a diluent only.
Figure 6B:
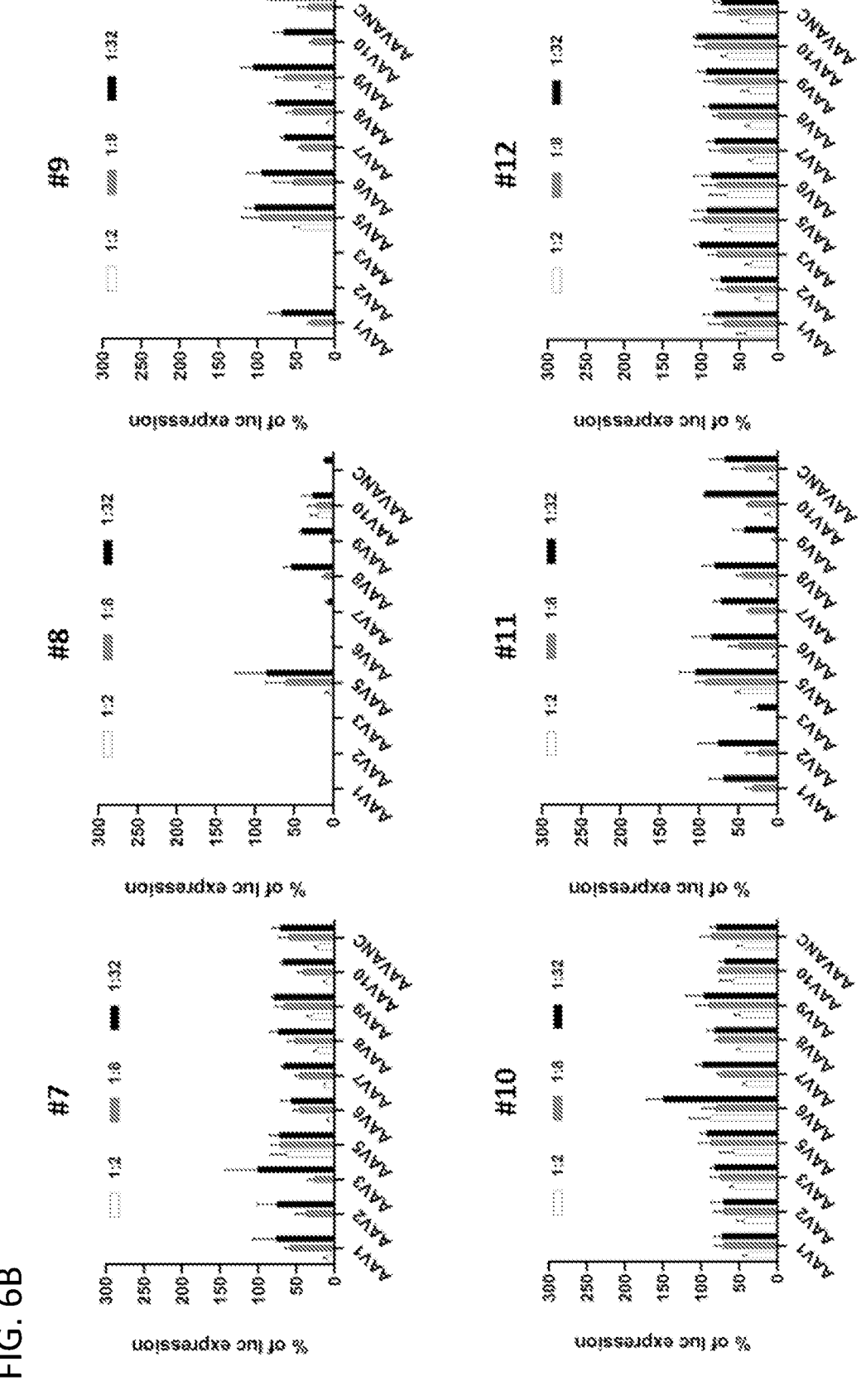
Figure 6C:
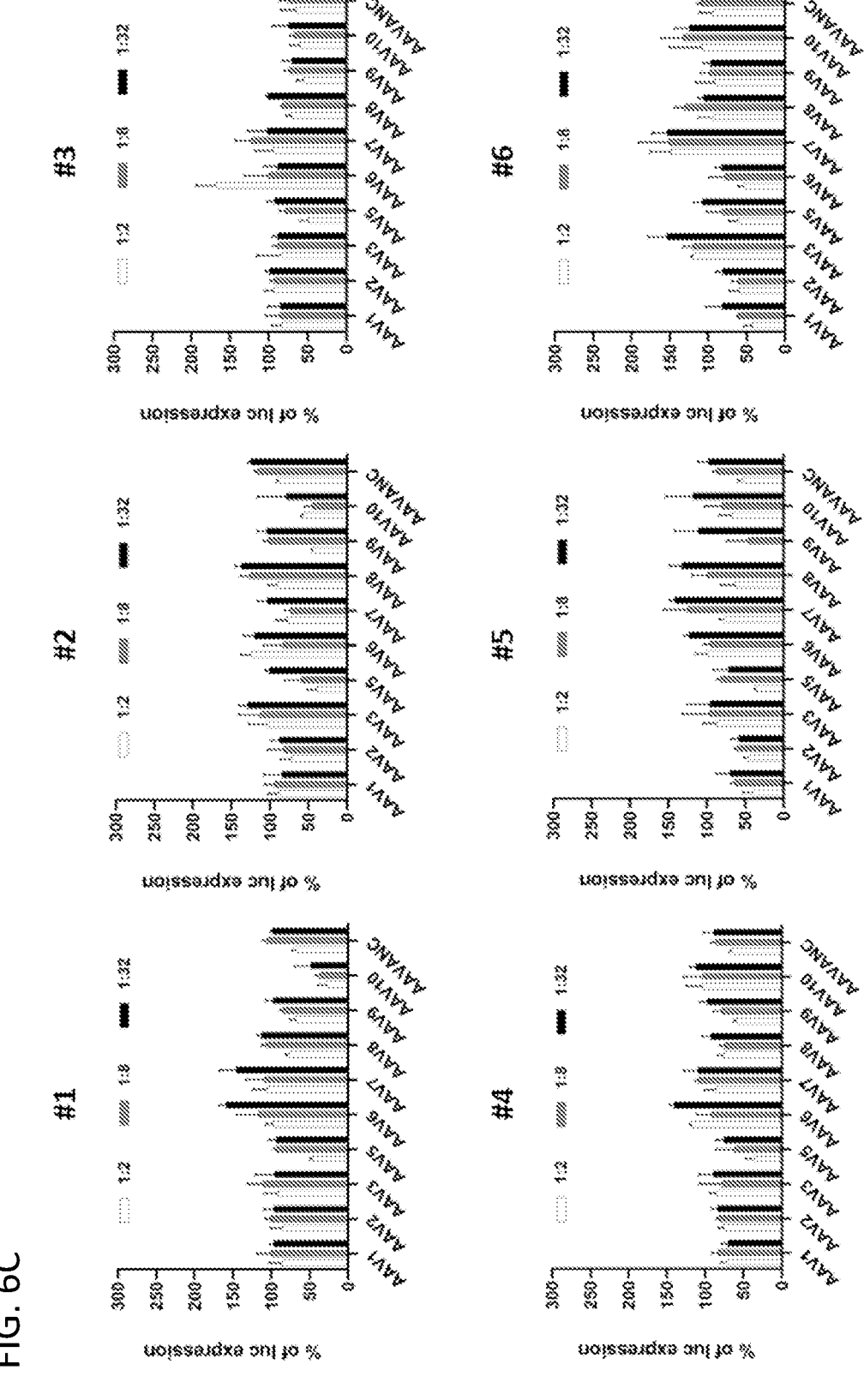
Figure 6D:
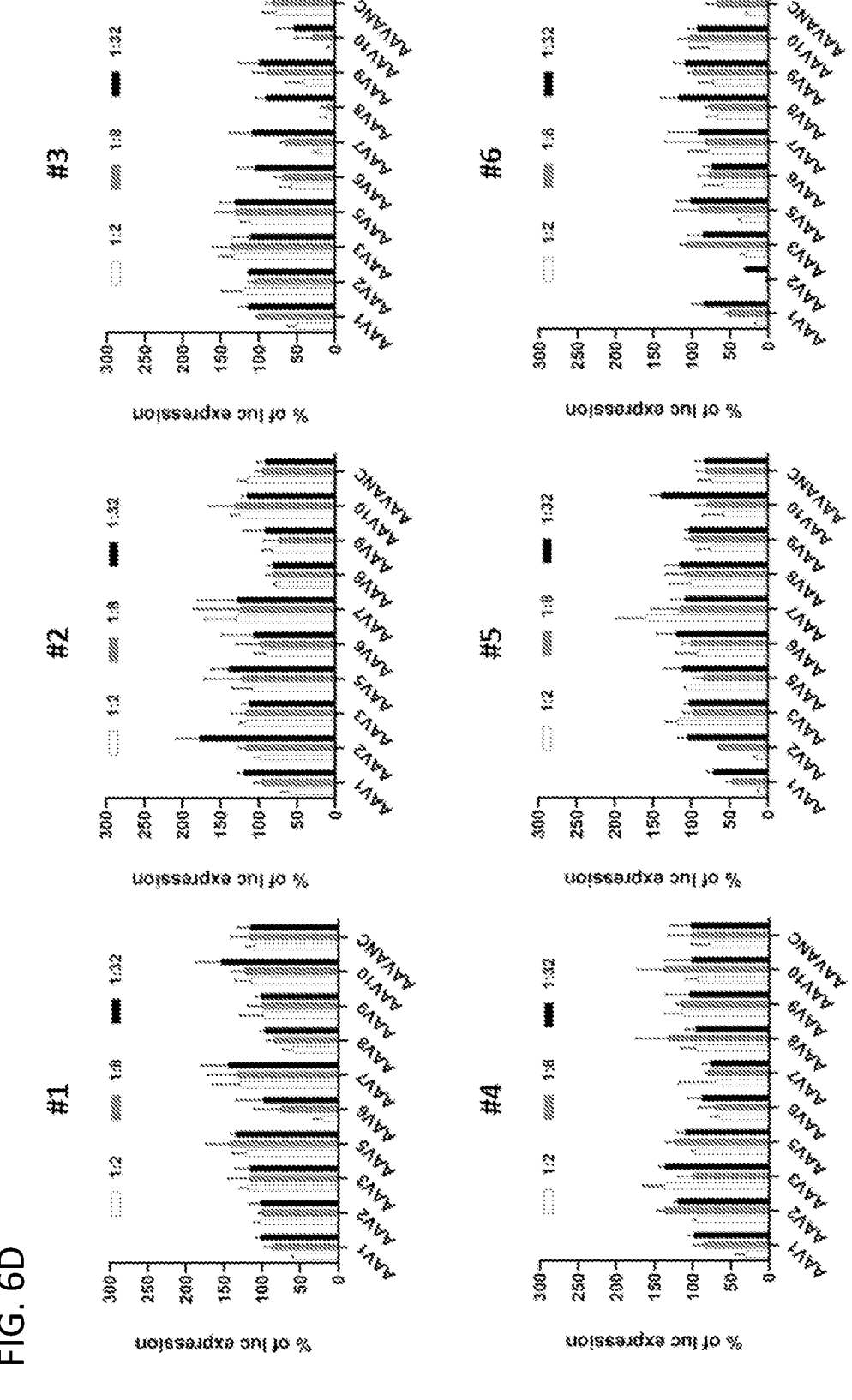
Figure 7A:
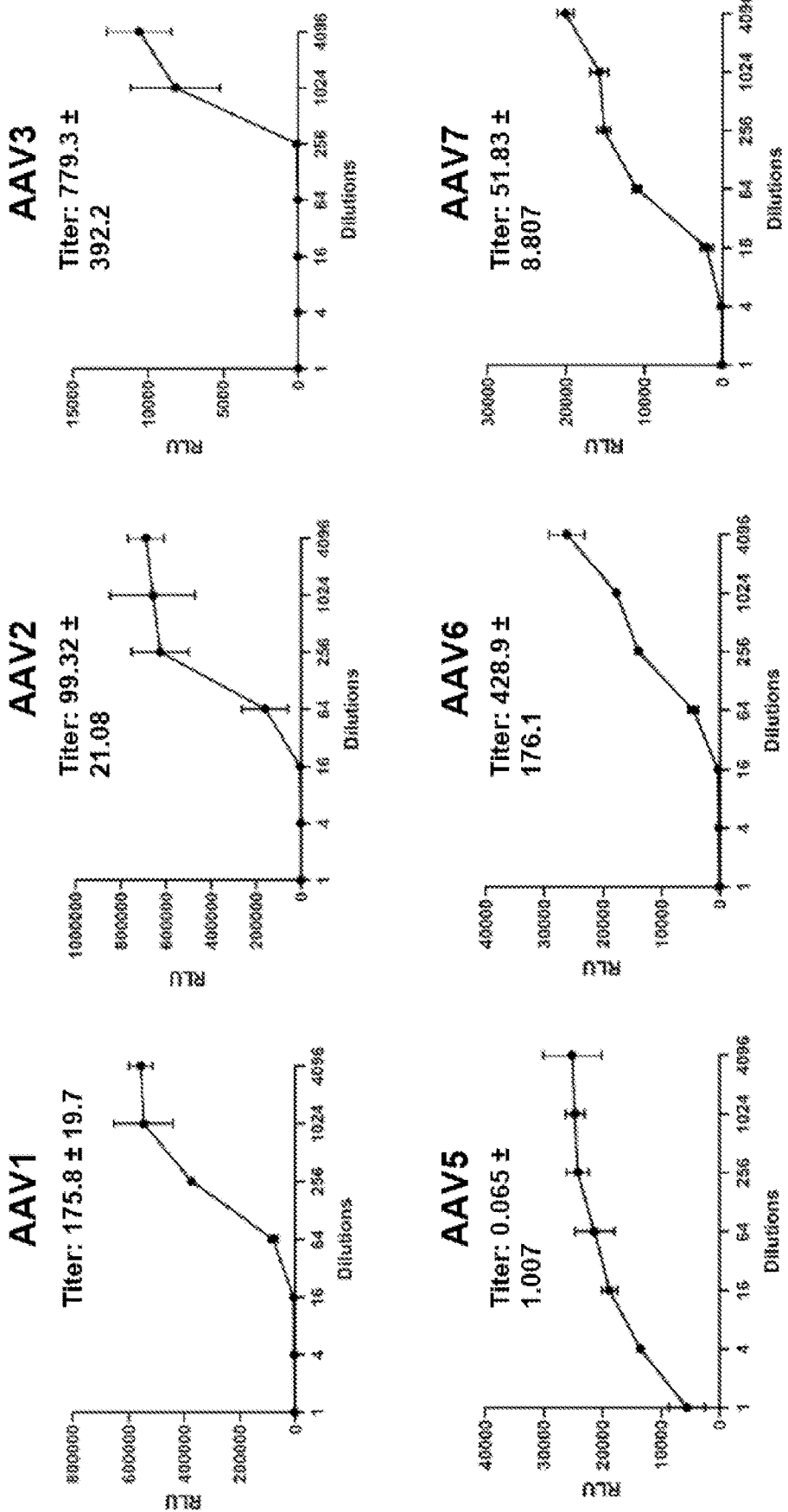
Figure 7B:
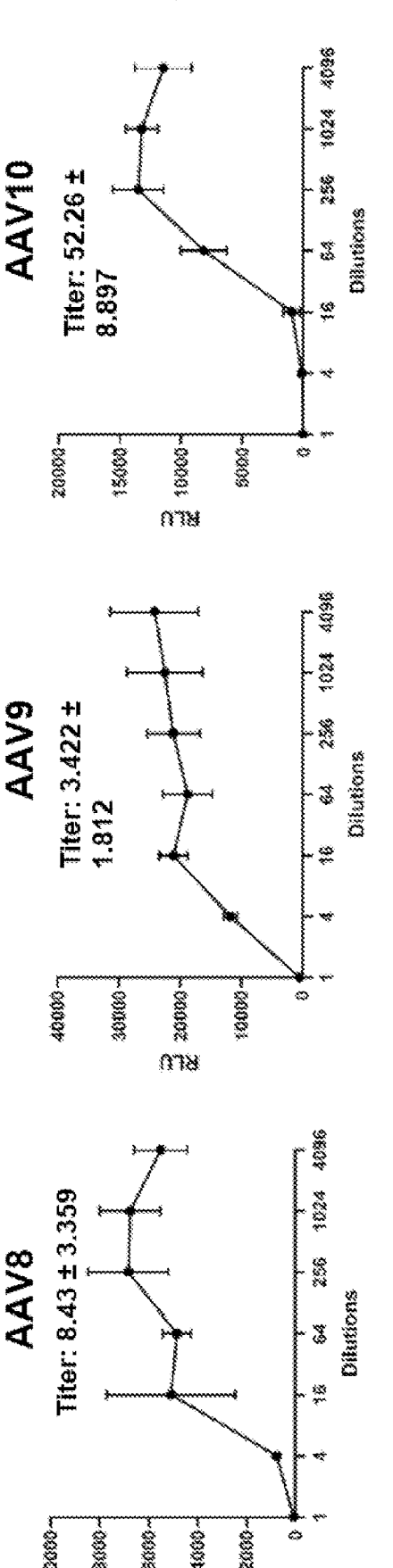
Figure 7C:
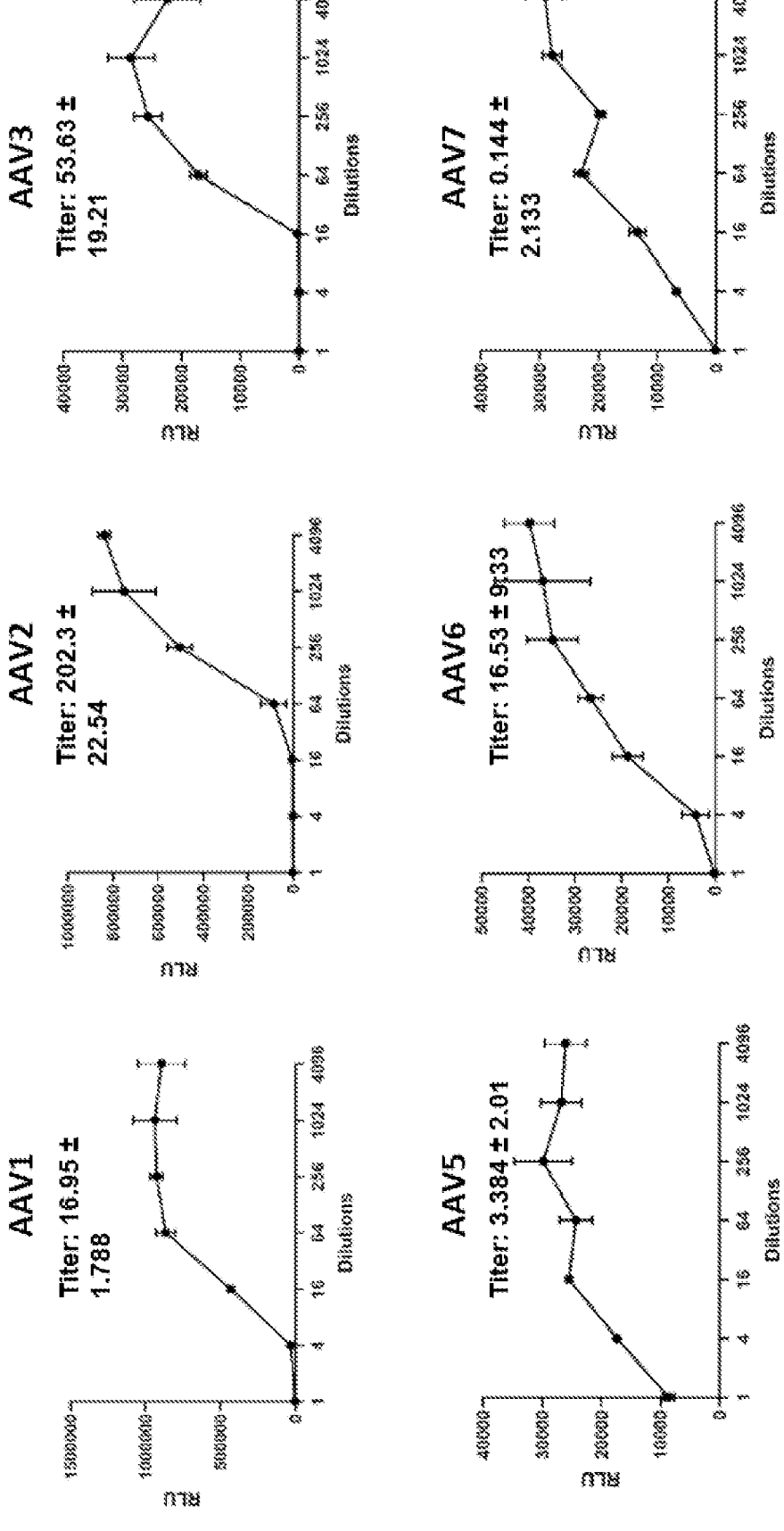
Figure 7E:
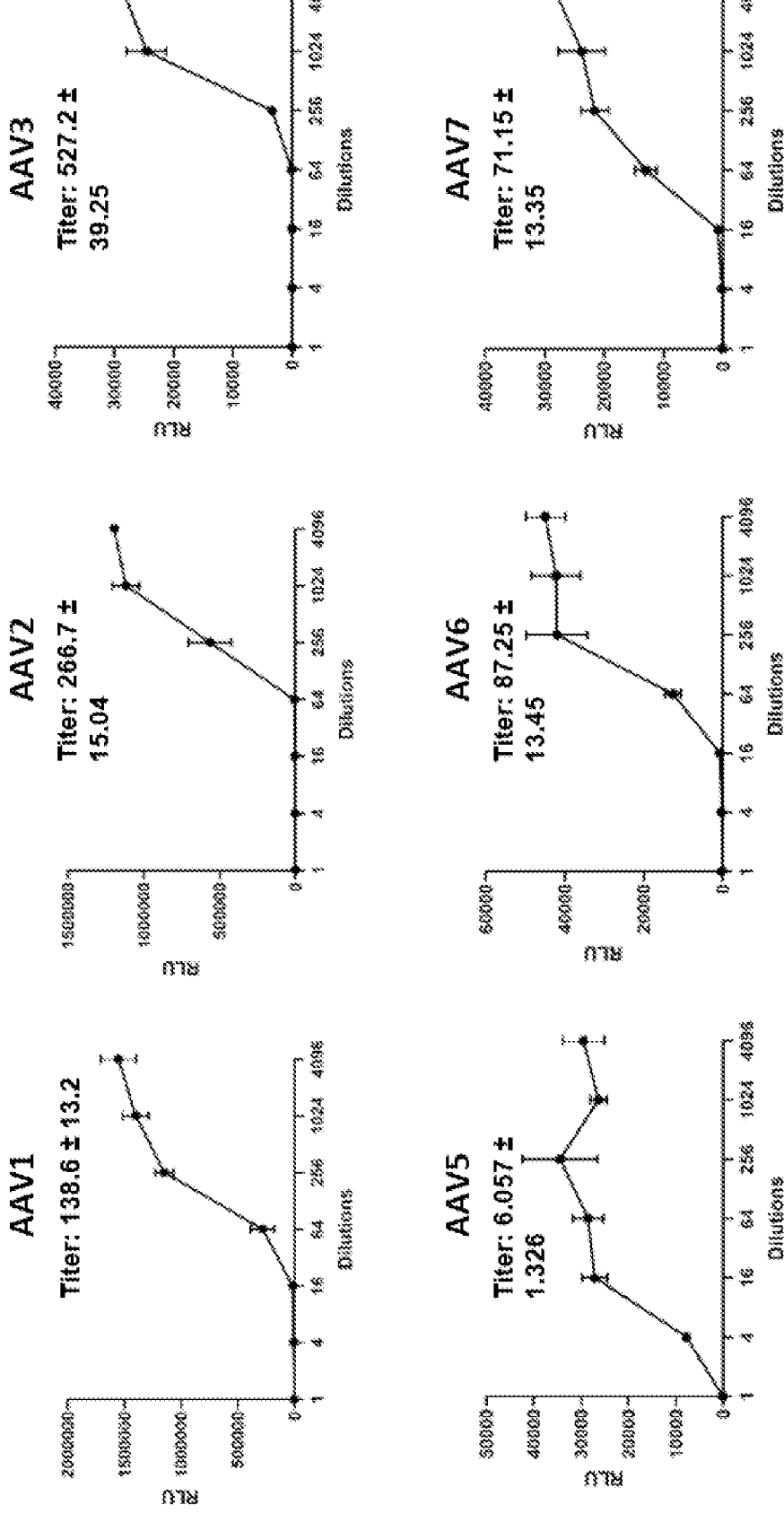
Figure 7G:
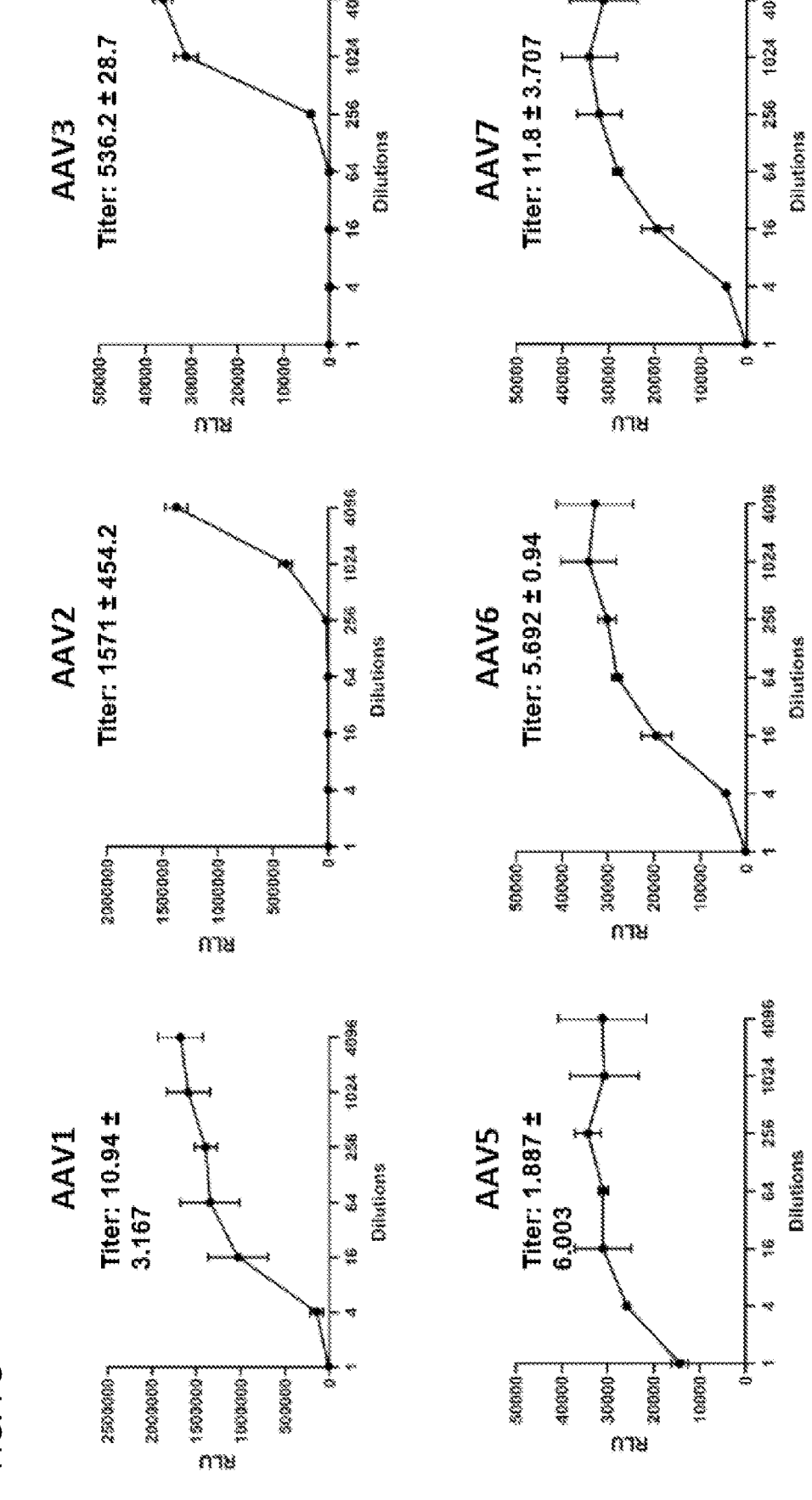
Figure 7H:
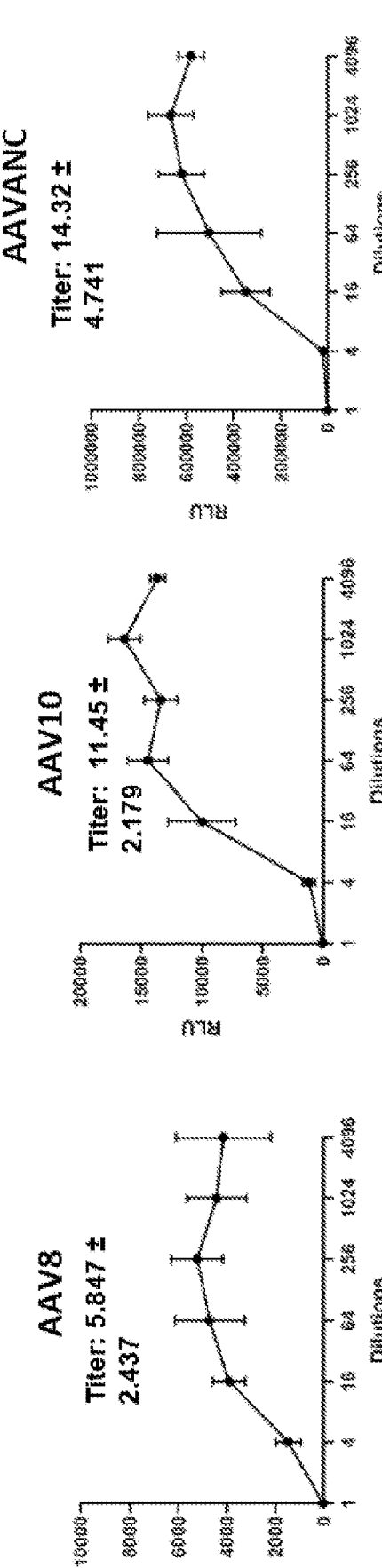
Figure 7I:
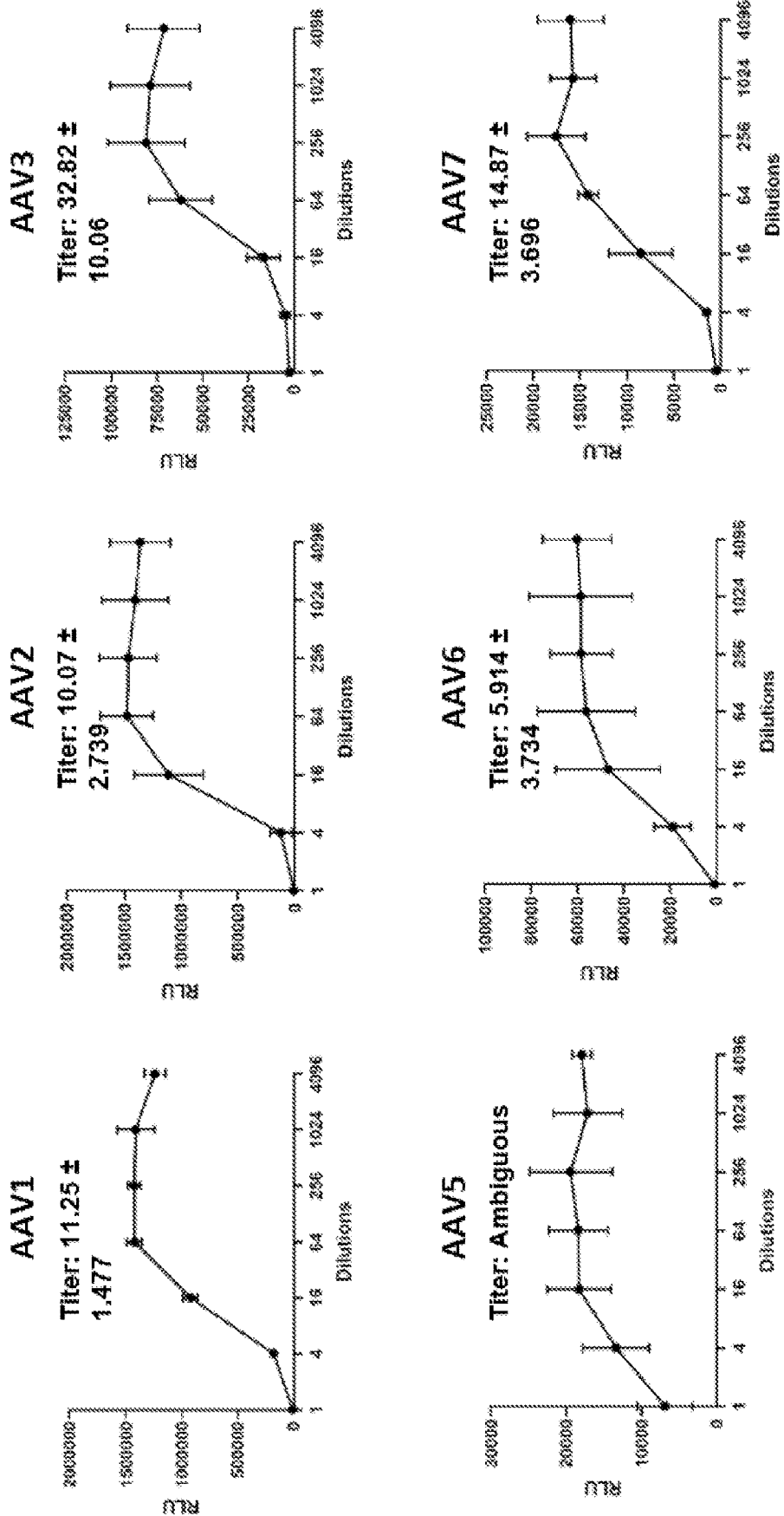
Figure 7J:
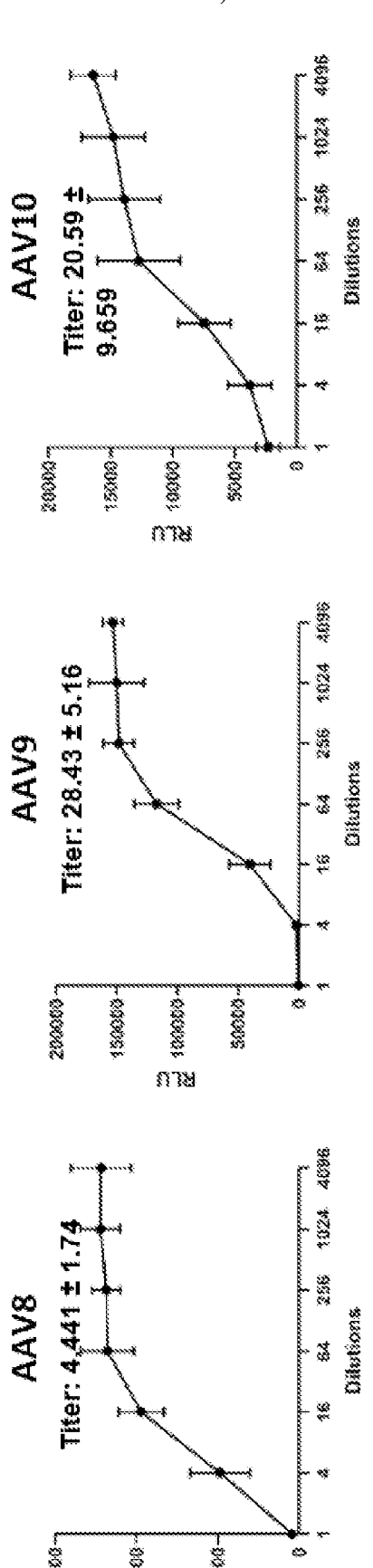
Figure 9A:
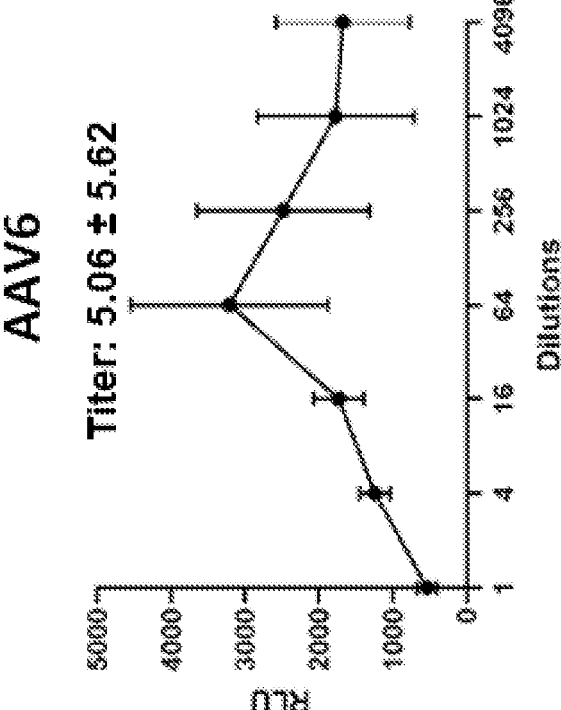
Figure 9B:
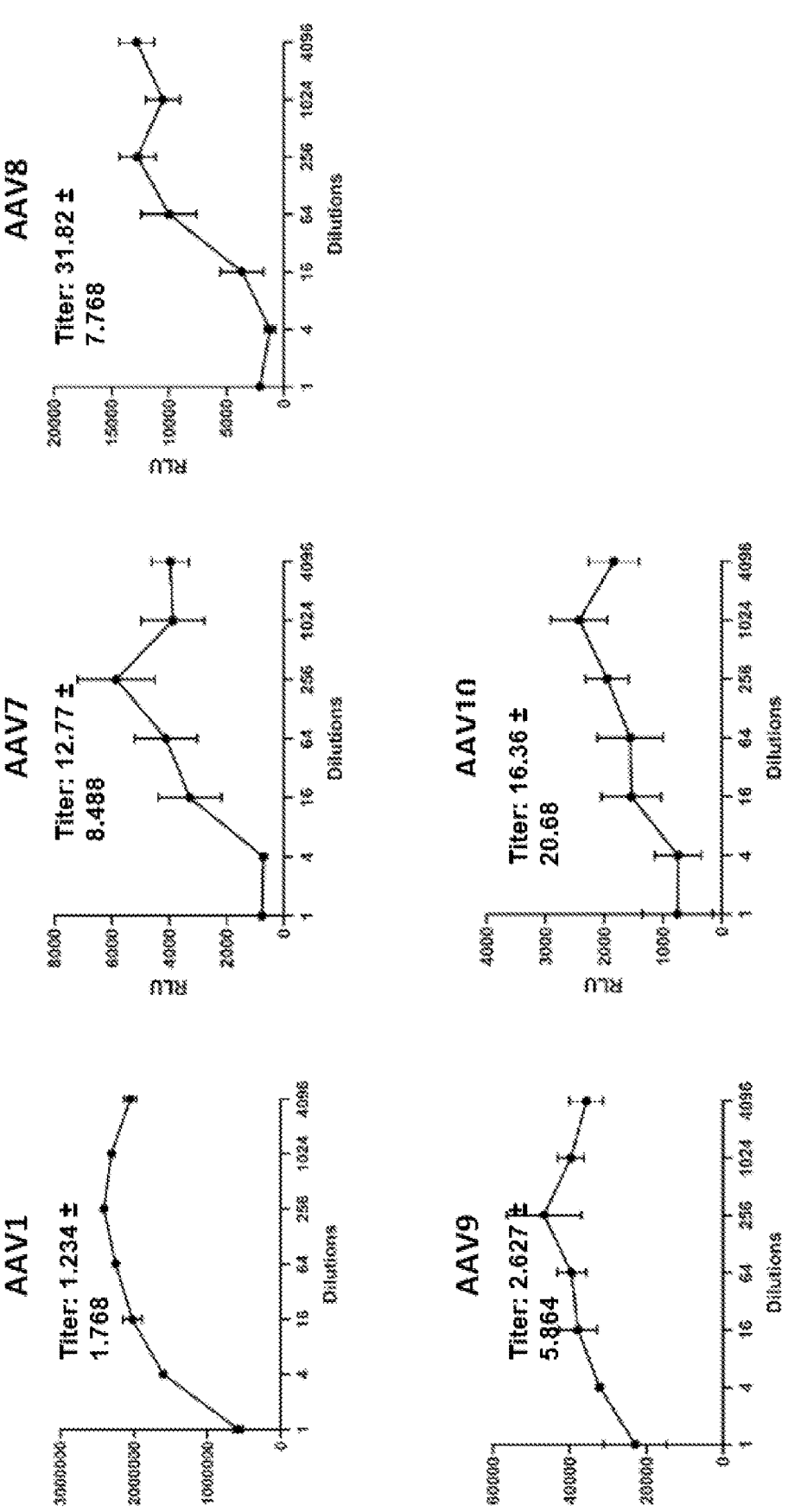
Figure 9E:
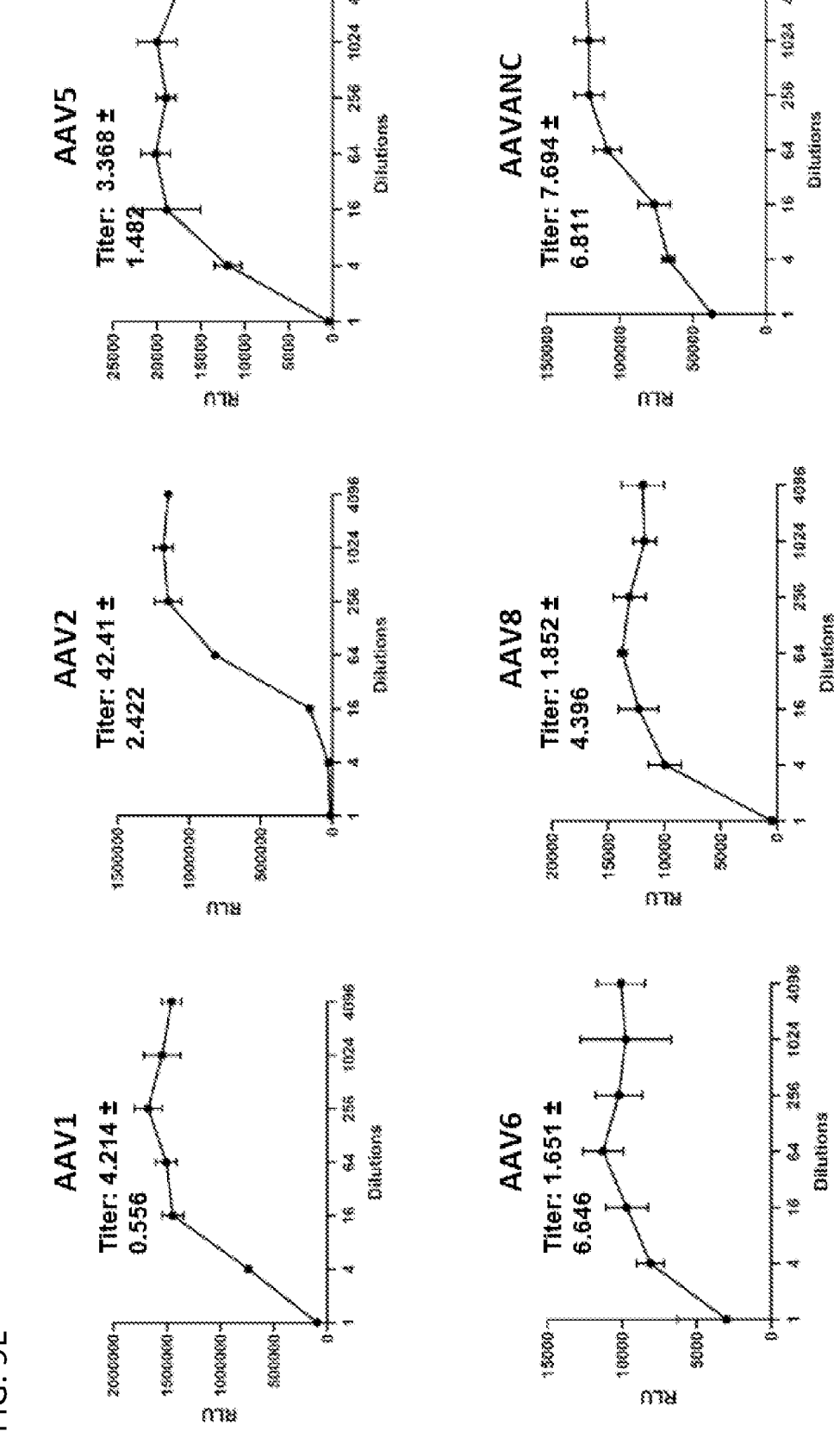

Results are shown in FIG. 4 and indicate that CC does not affect NAb titer because inhibition appears at the same dilution of the serum. NAb titer was calculated using Method 1, above.

Finally, the successful measurements of NAb titers using the protocol described above for three different AAV serotypes (AAV8, AAV6, and AAV3) was demonstrated with mouse serum collected from animals injected intramuscularly with corresponding AAVs. Results are shown in FIG. 5. NAb titer was calculated using Method 1, above.

In summary, this Example describes the validation of a universal protocol for analysis of AAV-specific NAb for commonly used serotypes.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method comprising:
providing an HEK293 cell responsive to an AMP-activated protein kinase (AMPK) inhibitor; and
infecting the cell with adeno-associated virus (AAV) in the presence of dorsomorphin.

2. The method of claim 1, wherein the AAV comprises AAV1, AAV2, AAV3, AAV5, AAV6, AAV7, AAV8, AAV9, AAV10, AAV Anc80L65, or AAVKLK.

3. The method of claim 1, wherein the AAV is an AAV vector.

4. The method of claim 3, wherein the AAV vector comprises a reporter gene.

5. The method of claim 4, wherein the reporter gene encodes luciferase.

6. The method of claim 1, wherein dorsomorphin is added up to 30 minutes, up to 40 minutes, up to 50 minutes, up to 60 minutes, up to 90 minutes, up to 120 minutes, or up to 180 minutes prior to the addition of AAV.

7. The method of claim 1, wherein dorsomorphin is added to the cell at a concentration of up to 4 μM, up to 6 μM, up to 8 μM, up to 10 μM, up to 15 μM, up to 20 μM, or up to 30 μM.

8. The method of claim 1, wherein the method further comprises infecting the cell with AAV in the presence of IL-6 or TNFα or both.

9. The method of claim 1, wherein the method further comprises adding a composition to the dorsomorphin-treated cell at the time of infecting the cell with AAV, wherein the composition comprises:
a composition known to comprise a neutralizing antibody (NAb) to AAV; or
a composition being tested for the presence of a NAb to AAV.

10. The method of claim 9, wherein the AAV is an AAV vector comprising a reporter gene.

11. The method of claim 9, wherein the composition comprises serum.

12. The method of claim 11, wherein the serum is serum from a human or an animal.

13. The method of claim 9, wherein adding a composition to the dorsomorphin-treated cell comprises:

adding a first dilution of the composition to a first sample of dorsomorphin-treated cells; and adding a second dilution of the composition to a second sample of dorsomorphin-treated cells.

14. The method of claim 9, wherein the method comprises determining an NAb titer within 72 hours of infecting the cell with AAV.

15. The method of claim 10, wherein the method comprises measuring the level of the reporter gene expressed by the cell.

16. The method of claim 10, wherein the reporter gene comprises luciferase.

17. The method of claim 15, wherein adding a composition to the dorsomorphin-treated cell comprises:

providing a plurality of samples of dorsomorphin-treated cells;

adding a plurality of serial dilutions of the composition across the plurality of samples, one serial dilution per sample; and determining the serial dilution at which 50% or greater inhibition of the reporter gene is observed.

* * * * *